(12) United States Patent
Cardosi et al.

(10) Patent No.: US 10,788,442 B2
(45) Date of Patent: Sep. 29, 2020

(54) ELECTROCHEMICAL TEST DEVICE

(71) Applicant: Inside Biometrics Limited, Dingwall (GB)

(72) Inventors: Marco Cardosi, Dingwall (GB); Stephanie Kirkwood, Dingwall (GB); Damian Baskeyfield, Dingwall (GB)

(73) Assignee: INSIDE BIOMETRICS INTERNATIONAL LIMITED, Dingwall (GB)

( * ) Notice: Subject to any disclaimer, the term of this patent is extended or adjusted under 35 U.S.C. 154(b) by 324 days.

(21) Appl. No.: 15/569,742

(22) PCT Filed: Apr. 27, 2016

(86) PCT No.: PCT/GB2016/051233
§ 371 (c)(1),
(2) Date: Oct. 26, 2017

(87) PCT Pub. No.: WO2016/174460
PCT Pub. Date: Nov. 3, 2016

(65) Prior Publication Data
US 2018/0143155 A1    May 24, 2018

(30) Foreign Application Priority Data

Apr. 30, 2015   (GB) .................................. 1507510.4

(51) Int. Cl.
*G01N 27/327*   (2006.01)
*C12Q 1/00*     (2006.01)
(Continued)

(52) U.S. Cl.
CPC ......... *G01N 27/3272* (2013.01); *C12Q 1/004* (2013.01); *C12Q 1/26* (2013.01);
(Continued)

(58) Field of Classification Search
CPC . C12Q 1/00; C12Q 1/02; C12Q 1/006; C12Q 1/34; C12Q 1/54; G01N 27/327;
(Continued)

(56) References Cited

U.S. PATENT DOCUMENTS 6,984,307 B2    1/2006  Sweig
2007/0295616 A1  12/2007  Harding et al.
(Continued)

FOREIGN PATENT DOCUMENTS

| EP | 2308991 A1 | 4/2011 |
| EP | 2317313 A1 | 5/2011 |
| EP | 2573190 A1 | 3/2013 |

OTHER PUBLICATIONS

International Search Report and Written Opinion dated Jul. 21, 2016 for corresponding International Patent Application No. PCT/GB2016/051233.
(Continued)

*Primary Examiner* — Gurpreet Kaur
(74) *Attorney, Agent, or Firm* — Tarolli, Sundheim, Covell & Tummino LLP

(57) ABSTRACT

An electrochemical test device for use in determining a concentration of each of a first analyte and a second analyte in a fluid sample is provided. The electrochemical test device comprises a set of electrodes including a first working electrode having sensing chemistry for the first analyte and a second working electrode having sensing chemistry for the second analyte, wherein the first analyte is lactate and the sensing chemistry for the lactate comprises lactate oxidase and an electron transfer agent, and wherein the sensing chemistry for the second analyte comprises a diaphorase, an electron transfer agent, an $NAD(P)^+$-dependent dehydrogenase and a cofactor for the $NAD(P)^+$-dependent dehydrogenase.

20 Claims, 12 Drawing Sheets

(51) Int. Cl.
*C12Q 1/32* (2006.01)
*C12Q 1/26* (2006.01)
*G01N 35/00* (2006.01)

(52) U.S. Cl.
CPC ........... *C12Q 1/32* (2013.01); *G01N 27/3271* (2013.01); *G01N 2035/00118* (2013.01)

(58) Field of Classification Search
CPC .... G01N 27/3272; G01N 27/40; G01N 27/48; G01N 27/26; G01N 27/10; G01N 27/06
See application file for complete search history.

(56) References Cited

U.S. PATENT DOCUMENTS

| | | | | |
|---|---|---|---|---|
| 2010/0096276 | A1* | 4/2010 | Kojima | C12Q 1/005 205/777.5 |
| 2010/0267161 | A1* | 10/2010 | Wu | C12Q 1/001 436/149 |
| 2013/0075276 | A1* | 3/2013 | Hoashi | C12Q 1/004 205/777.5 |

OTHER PUBLICATIONS

GB Search Report dated Feb. 1, 2016 for corresponding GB Patent Application No. 1507510.4.

Mizutani F., et al., "L-Malate-sensing electrode based on malate dehydrogenase and NADH oxidase", pp. 145-150, Analytica Chimica, vol. 245, 1991 (See in particular the Experimental Section at pp. 146-147).

Katrlik J., et al., "Biosensors for L-malate and L-lactate based on solid binding matrix", pp. 193-200, Analytica Chimica, vol. 379, 1999 (See in particular the Experimental Section at pp. 194-195).

Kakehi N et al., "A Novel wireless glucose sensor employing direct electron transfer principle based enzyme fuel cell", "Biosensors and Bioelectronics", vol. 22, Jan. 1, 2007, pp. 2250-2255.

* cited by examiner

|  | Glycerol (µM) | Lactate (mM) |
|---|---|---|
| Donor 1 | 70 | 5.91 |
| Donor 2 | 450 | 5.84 |

# ELECTROCHEMICAL TEST DEVICE

RELATED APPLICATIONS

The present application is a U.S. National Stage application under 35 USC 371 of PCT Application Serial No. PCT/GB2016/051233, filed on 28 Apr. 2016; which claims priority from GB Patent Application No. 1507510.4, filed 30 Apr. 2015, the entirety of both of which are incorporated herein by reference.

TECHNICAL FIELD

The present invention relates to electrochemical test devices such as test strips for determining the concentration of one or more analytes in a fluid sample. In particular, the present invention relates to sensing chemistry for such electrochemical test devices.

BACKGROUND

The detection and measurement of substances, chemicals, or analytes in a bodily fluid sample is useful in a variety of applications, such as in fitness monitors or in the medical device industry. For example, an individual may choose to monitor a concentration of an analyte such as glycerol in his or her bloodstream in order to determine whether or not a chosen fitness regime is effective. Glycerol is a fitness related analyte associated with lipolysis and fat breakdown from stored body fat.

As another example, people with diabetes need to regularly monitor the concentration of glucose in their bloodstream in order to determine if they are in need of glucose or insulin or other diabetes medication. Diagnostic devices and kits have been developed over the years to allow a diabetic individual to autonomously determine the concentration of glucose in their bloodstream, in order to better anticipate the onset of hyperglycaemia or hypoglycaemia and take any necessary action.

When trying to ascertain a level of an analyte in, for example, a blood sample, an individual will typically perform a finger stick using a lancing device to extract a small drop of blood from a finger or alternative site. An electrochemical test device, which is often a test strip, is then inserted into a diagnostic meter, and the sample is applied to the test strip. Through capillary action, the sample flows through a capillary channel across a measurement chamber of the device and into contact with one or more electrodes or conductive elements coated with sensing chemistry for interacting with a particular analyte or other specific chemical (for example glucose) in the blood sample. The magnitude of the reaction is dependent on the concentration of the analyte in the blood sample. The diagnostic meter may detect the current generated by the reaction of the sensing chemistry with the analyte, and the result can be displayed to the individual.

Typically, such electrochemical test devices have a set of electrodes such as a counter/reference electrode and one or more working electrodes. Sensing chemistry is used which is typically tailored to the particular analyte or biometric of interest. An enzymatic electrode is a combination of an enzyme and an electrochemical transducer. The direct transfer of electrons between the enzyme and the electrode is generally not easy to achieve and so an electron transfer agent (or mediator) is sometimes used to carry electrons between the enzyme and the electrode to facilitate the electrocatalysis. For example, when measuring the concentration of glucose in a sample, a glucose oxidase or a glucose dehydrogenase enzyme can be used in conjunction with a mediator such as potassium ferricyanide. When detecting other analytes, different enzymes may be used, such as β-hydroxybutyrate dehydrogenase for measuring the ketone body β-hydroxybutyrate.

The NAD(P)$^+$-dependent dehydrogenases, such as glycerol dehydrogenase, require nicotinamide adenine dinucleotide (either in its oxidized form, NAD(P)$^+$ or reduced form, NAD(P)H) as a cofactor for the dehydrogenase. Since the dehydrogenases release NAD(P)$^+$/NAD(P)H from active sites reversibly, NAD(P)$^+$/NAD(P)H may function as the electron transfer agent in the dehydrogenase-modified electrodes. The direct oxidation of NAD(P)H at a carbon working electrode requires a large positive overpotential (for example 0.55 V) and so electrochemically active interferents may transfer electrons to the electrode, thereby interfering with the measurement of an analyte.

In a healthy individual, for some analytes such as glycerol or β-hydroxybutyrate the concentrations of the analytes may be very low. Insensitive or inaccurate electrochemical test devices may take unreliable measurements of the concentration of such analytes. For measurements of some analytes, such as glycerol or β-hydroxybutyrate, sensitive electrochemical test devices are desired.

An aspect of the present invention seeks to provide an improved electrochemical test device for determining the concentration of analytes in a fluid sample. Another aspect of the present invention seeks to provide an improved method for determining the concentration of analytes in a fluid sample.

SUMMARY

An electrochemical test device for determining a concentration of each of a first analyte and a second analyte in a fluid sample is disclosed. The electrochemical test device may comprise a set of electrodes including a first working electrode having sensing chemistry for the first analyte and a second working electrode having sensing chemistry for the second analyte. The first analyte may be lactate. The sensing chemistry for the lactate may comprise lactate oxidase. The sensing chemistry for the lactate may comprise an electron transfer agent. The sensing chemistry for the second analyte may comprise a diaphorase. The sensing chemistry for the second analyte may comprise an electron transfer agent. The sensing chemistry for the second analyte may comprise an NAD(P)$^+$-dependent dehydrogenase. The sensing chemistry for the second analyte may comprise a cofactor for the NAD(P)$^+$-dependent dehydrogenase.

An apparatus is disclosed. The apparatus may be configured to determine the concentration of an analyte in a fluid sample applied to an electrochemical test device as described herein.

An electrochemical test device for use in determining a concentration of a first analyte in a fluid sample and a concentration of a second analyte in the fluid sample is disclosed. The device may comprise a set of electrodes comprising a first working electrode, a second working electrode and a counter/reference electrode. The first working electrode may be provided with first sensing chemistry for the first analyte. The first sensing chemistry may include a first electron transfer agent. The second working electrode may be provided with second sensing chemistry for the second analyte. The second sensing chemistry may include a second electron transfer agent. The counter/reference electrode may be provided with a third electron transfer agent. The first electron transfer agent may have a first standard redox potential. The second electron transfer agent may have a second standard redox potential. The third electron transfer agent may have a third standard redox potential. The third standard redox potential may be higher than the second standard redox potential by at least 0.2V. The first standard redox potential may be substantially the same as the third standard redox potential.

A method is disclosed for determining a concentration of a first analyte in a fluid sample and a concentration of a second analyte in the fluid sample, wherein an electrochemical test device is used. The electrochemical test device may comprise a set of electrodes comprising a first working electrode, a second working electrode, and a counter/reference electrode. The first working electrode may be provided with first sensing chemistry for the first analyte. The first sensing chemistry may include a first electron transfer agent. The second working electrode may be provided with second sensing chemistry for the second analyte. The second sensing chemistry may include a second electron transfer agent. The counter/reference electrode may be provided with a third electron transfer agent. The first electron transfer agent may have a first standard redox potential. The second electron transfer agent may have a second standard redox potential. The third electron transfer agent may have a third standard redox potential. The third standard redox potential may be higher than the second standard redox potential by at least 0.2V. The first standard redox potential may be substantially the same as the third redox potential. The method may comprise operating in a fuel cell mode for a first period in which the difference between the second standard redox potential and the third standard redox potential causes current to flow from the second working electrode to the counter/reference electrode. The first period may serve as a poise delay period for the first working electrode. The method may further comprise, after the first time period, applying a potential difference for a second time period between the first working electrode and the counter/reference electrode. The method may further comprise determining the concentration of the second analyte based on an output signal generated from the current that flows between the second working electrode and the counter/reference electrode in the first time period. The method may further comprise determining the concentration of the first analyte based on an output signal generated from the current that flows between the first working electrode and the counter/reference electrode in the second time period.

An apparatus is disclosed. The apparatus may be for determining a concentration of a first analyte in a fluid sample and a concentration of a second analyte in the fluid sample. The apparatus may comprise circuitry for receiving an output signal generated from a fluid sample. The apparatus may further comprise a memory storing instructions to perform a method as described herein. The apparatus may further comprise a processor configured to perform the instructions stored in the memory.

A machine-readable medium is disclosed. The machine-readable medium may have instructions stored thereon. The instructions may be configured such that when read by a machine the instructions cause a method as described herein to be carried out.

Further optional features will be appreciated from the following description.

BRIEF DESCRIPTION OF THE DRAWINGS

Illustrative embodiments of the present disclosure will now be described, by way of example only, with reference to the drawings. In the drawings.

Throughout the description and the drawings, like reference numerals refer to like parts.

DESCRIPTION

Figure 1:
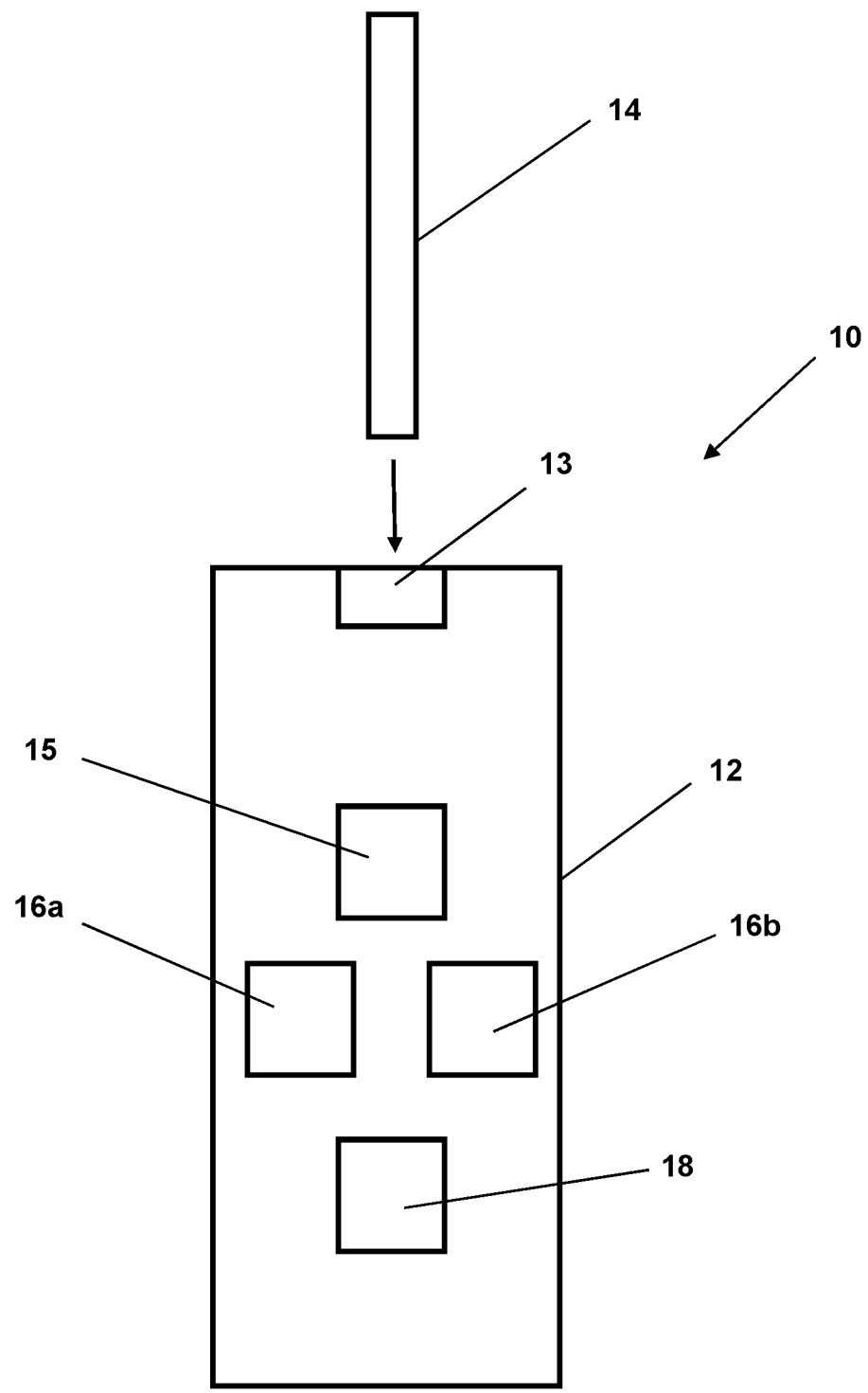
FIG. 1 shows a test strip-meter system.

The present invention seeks to provide an improved electrochemical test device for determining a concentration of one or more analytes in a fluid sample. Whilst various embodiments of the invention are described below, the invention is not limited to these embodiments, and variations of these embodiments may be made without departing from the scope of the invention.

Throughout this specification, reference is made to directional terms such as "above" and "below", or "upper" and "lower". References made to such terms are purely indicative of relative positions of the features of embodiments disclosed herein. For example, wherever there is mention of a cover above a spacer layer and an insulator layer below the spacer layer, it should be understood that the cover and the insulator layer are formed on opposite sides of the spacer layer. That is, directional terms such as those described herein do not refer to a direction relative to a viewpoint of an observer, but instead should be considered in all aspects as relative terms.

Various additional details of aspects of electrochemical test devices are described in the following commonly assigned patent applications (denoted collectively herein as the "related applications"). These related applications include the International patent application No. PCT/GB2016/051229, entitled "Electrochemical test device" filed on 28 Apr. 2016; the International patent application No. PCT/GB2016/051230, entitled "Electrochemical test device" filed on 28 Apr. 2016; the International patent application No. PCT/GB2016/051231, entitled "Electrochemical test device" filed on 28 Apr. 2016; the International patent application No. PCT/GB2016/051228, entitled "Electron transfer agent" filed on 28 Apr. 2016; and the International patent application No. PCT/GB2016/051232, entitled "Electrochemical test device" filed on 28 Apr. 2016. The content of each of these related applications is hereby incorporated by reference herein in its entirety for all purposes.

The term "alkyl", used alone or as part of a larger moiety, refers to a straight or branched chain aliphatic group having from 1 to 12 carbon atoms. The alkyl group therefore has 1, 2, 3, 4, 5, 6, 7, 8, 9, 10, 11 or 12 carbon atoms. For purposes of the present disclosure, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

The term "amine" may refer to a primary, secondary or tertiary amine. The amine will generally be NRR'R", where R, R' and R" are each selected from hydrogen or alkyl. Any suitable alkyl group may be used. Preferred alkyl group will be $C_1$, $C_2$, $C_3$, $C_4$, $C_5$, $C_6$. Preferably, an amine is $NH_3$.

The term "heteroaryl" means a monocyclic or bicyclic radical of 5 to 12 ring atoms having at least one aromatic ring containing one, two, or three ring heteroatoms selected from N, O or S, the remaining ring atoms being C. The attachment point of the heteroaryl radical may be via the heteroatom. The heteroaryl rings may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The term "halide" refers to a substituent which is fluoro, chloro, bromo or iodo.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

An electron transfer agent (or redox mediator) is an agent for transferring electrons between an analyte or an analyte-reduced or analyte-oxidized enzyme and an electrode, either directly, or via one or more additional electron transfer agents.

An electron transfer agent as disclosed herein may be distinguishable by its standard redox potential i.e. a standard hydrogen electrode (SHE) at Standard Temperature and Pressure (25° C. and 1 atm).

An electrochemical test device for use in determining a concentration of each of a first analyte and a second analyte in a fluid sample is disclosed. The electrochemical test device comprises a set of electrodes including a first working electrode having sensing chemistry for the first analyte and a second working electrode having sensing chemistry for the second analyte. The first analyte is lactate and the sensing chemistry for the lactate comprises lactate oxidase and an electron transfer agent. The sensing chemistry for the second analyte comprises a diaphorase, an electron transfer agent, an $NAD(P)^+$-dependent dehydrogenase and a cofactor for the $NAD(P)^+$-dependent dehydrogenase.

The electrochemical test device is thus able to determine a concentration of lactate in a fluid sample. The electrochemical test device is also able to determine a concentration on an analyte using an $NAD(P)^+$-dependent dehydrogenase-based reaction.

The diaphorase may be any suitable diaphorase. For example, the diaphorase may be an NADPH:acceptor oxidoreductase (NADPH dehydrogenase of the class EC 1.6.99.1). The diaphorase may be an NADH:acceptor oxidoreductase (NADH dehydrogenase of the class EC 1.6.99.3). The diaphorase may be an NADH:(quinone acceptor) oxidoreductase (NADH dehydrogenase (quinone) of the class EC 1.6.99.5).

The cofactor may be nicotinamide adenine dinucleotide ($NAD^+$). The cofactor may be nicotinamide adenine dinucleotide phosphate (NADP+).

The second analyte may be glycerol and the $NAD(P)^+$-dependent dehydrogenase may be glycerol dehydrogenase. The second analyte may be β-hydroxybutyrate and the $NAD(P)^+$-dependent dehydrogenase may be β-hydroxybutyrate dehydrogenase. The second analyte may be glucose and the $NAD(P)^+$-dependent dehydrogenase may be $NAD^+$-glucose dehydrogenase.

The electron transfer agent for the first working electrode and the electron transfer agent for the second working electrode may be different electron transfer agents.

The set of electrodes may include a counter/reference electrode provided with a third electron transfer agent. The electron transfer agent for the first working electrode (the "first" electron transfer agent) may have a first standard redox potential. The electron transfer agent for the second working electrode (the "second" electron transfer agent) may have a second standard redox potential. The third electron transfer agent may have a third standard redox potential. The third standard redox potential may be higher than the second standard redox potential by at least 0.2V. That is, the value of the third standard redox potential minus the value of the second standard redox potential may have a magnitude that is greater than or equal to 0.2V. The first standard redox potential may be substantially the same as the third standard redox potential. "Substantially the same" in the context of this electron transfer agent provided at the counter/reference electrode means having a standard redox potential which is within 0.1V of the first standard redox potential.

Preferably the third electron transfer agent is a reversible or quasi-reversible electron transfer agent as measured by cyclic voltammetry. The third standard redox potential may be higher than the second standard redox potential by at least 0.3V. Preferably, the third standard redox potential is be higher than the second standard redox potential by at least 0.4V. The third standard redox potential may be in the range of −0.12V to 0.58V. The second standard redox potential may be in the range of −0.52V to 0.18V. Preferably, the first electron transfer agent is the same as the third electron transfer agent.

The electron transfer agent for the first working electrode may be a ferricyanide anion. For example, the ferricyanide anion may be potassium ferricyanide, or potassium hexacyanoferrate(III) (Red Prussiate of Potash, Prussian Red). The sensing chemistry for the first working electrode may be disposed in at least one layer. Each layer may comprise the lactate oxidase and the electron transfer agent for the first working electrode.

The sensing chemistry for the first working electrode may be disposed in two layers.

The sensing chemistry for the second working electrode may be disposed in at least one layer. Each layer may comprise the diaphorase, the electron transfer agent for the second working electrode, the NAD(P)$^+$-dependent dehydrogenase and the cofactor for the NAD(P)$^+$-dependent dehydrogenase.

The sensing chemistry for the second working electrode may be disposed in layers including a layer adjacent the second working electrode. The layer adjacent the second working electrode may comprise the diaphorase. The layer adjacent the second working electrode may comprise the electron transfer agent.

The layers may include a layer which is not adjacent the second working electrode. The layer which is not adjacent the second working electrode may comprise the NAD(P)$^+$-dependent dehydrogenase. The layer not adjacent the second working electrode may also comprise the cofactor.

The layers of sensing chemistry for the second working electrode may be disposed in two layers.

The electron transfer agent for the second working electrode may be ruthenium hexaammine trichloride.

The electron transfer agent for the second working electrode may be a naphthoquinone derivative.

The electron transfer agent for the first working electrode may be a ferricyanide anion and the electron transfer agent for the second working electrode may be ruthenium hexaammine trichloride.

The electron transfer agent for the first working electrode may be a ferricyanide anion and the electron transfer agent for the second working electrode may be ruthenium pentaammine chloride.

The second working electrode may be positioned nearer the entrance to the sample introduction chamber of the electrochemical test device than the first working electrode.

The electron transfer agent for the second working electrode may be a ruthenium- or osmium-based electron transfer agent. The ruthenium- or osmium-based electron transfer agent may be a complex of formula (1),

$$[M(A)_x(B)_y](X)_n \qquad (1)$$

wherein M is ruthenium or osmium, A is an amine ligand, each B is a ligand different to A, x is an integer selected from 1 to 5, y is an integer selected from 1 to 5, x+y is 6 or 8, n is an integer selected from 1 to 6, and X is any suitable counterion.

M may be ruthenium. For example, M may be Ru(II) or Ru(III). The oxidation state of the metal M in the complex may be selected to be 2+, 3+ or 4+.

A may be NRR'R", wherein R, R' and R" are independently selected from hydrogen or alkyl. A may be NH$_3$. It will be appreciated that when x is two or more, all "A" may be the same.

Each B is a ligand different to A. It will be appreciated that when y is 2 or more, B may be the same or different. B may be independently selected from a halide or optionally substituted heteroaryl. When B is an optionally substituted heteroaryl, the heteroaryl may be optionally substituted with an optionally substituted C$_{1-6}$ alkyl. B may be a halide, and the halide may be selected from the group consisting of F$^−$, Cl$^−$, Br$^−$, I$^−$. B may be chloride. B may be pyridyl, or 4-methyl pyridyl.

It will be appreciated that A and B may be selected such that the overall charge on the complex of formula (1) is selected from the group +2, +1, 0, −1, −2 and −3.

The counterion X may be a counterion selected to lead to the charge neutrality of [M(A)$_x$(B)$_y$]. The counterion X may be selected from F$^−$, Cl$^−$, Br$^−$, I$^−$, PF$_6^−$.

The ruthenium complex may be [Ruthenium$^{III}$(NH$_3$)$_5$Cl]X (ruthenium pentaammine chloride). The ruthenium complex may be [Ruthenium$^{III}$(NH$_3$)$_5$Cl].2Cl.

The ruthenium- or osmium-based electron transfer agent may be a ruthenium-based electron transfer agent. The concentration of the ruthenium-based electron transfer agent in the sensing chemistry for the second electrode may be from 8% to 15% by weight before drying of the sensing chemistry.

Transition metal complexes of the present disclosure can be soluble in water or other aqueous solutions. In general, the transition metal complexes can be made soluble in aqueous solvents by having an appropriate counterion or ions, X. The solubility of the transition metal complex may be greater than about 0.025M at 25° C. in water.

The sensing chemistry may comprise between about 0.3%-2% (w/w) diaphorase. The sensing chemistry may comprise about 1% (w/w) diaphorase.

The diaphorase may be dissolved in a buffer such as, for example, phosphate or citrate. The buffer may be Tris buffer. The pH of the buffer may be about 7.

The sensing chemistry may comprise a phosphate or Tris buffer. The pH of the buffer may be in the range of about 6.5-7.5. For example, the pH of the buffer may be about 7. The pH of the buffer may be in the range of about 9.5-11. For example, the pH of the buffer may be about 10.5. The buffer may be of any suitable pH.

The diaphorase may have an enzyme activity range of from about 75 kU to 200 kU per 100 grams composition. The enzyme activity range is selected so that the analyte current does not depend on the level of enzyme activity in the composition and to avoid solubility issues for too high levels of diaphorase.

The sensing chemistry may comprise between about 0.07%-0.13% (w/w) flavin mononucleotide (FMN). The sensing chemistry may comprise 0.1% (w/w) FMN.

The sensing chemistry may comprise about 0.5%-3.5% (w/w), or 2.5%-3.5% (w/w), hydroxyethyl cellulose (HEC). The sensing chemistry may comprise 3% HEC.

In the context used herein, "about" may refer to a variation of ±10% of the numerical value.

The electron transfer agent for the first working electrode and the electron transfer agent for the second working electrode may have standard redox potentials which are substantially the same. "Substantially the same" in the context of these electron transfer agents means having a standard redox potential which is within 0.1V of each other. The electron transfer agent for the first working electrode and the electron transfer agent for the second working electrode may be the same electron transfer agent.

The electron transfer agent for the first working electrode and the electron transfer agent for the second working electrode may comprise a suitable quinone, for example a naphthoquinone derivative. The naphthoquinone derivative may be a 1,2 naphthoquinone derivative or a 1,4 naphthoquinone derivative. For example, the electron transfer agent may comprise 1,4 naphthoquinone-2-mercapto methyl carboxylic acid which has a standard redox potential of around −0.355V. The electron transfer agent may comprise 1,4 naphthoquinone-2-mercapto benzoic acid, which has a standard redox potential of around −0.345V. The electron transfer agent may comprise 1,2 naphthoquinone-4-sulphonate, which has a standard redox potential of around −0.214V. The electron transfer agent may comprise 1,4 naphthoquinone-2-mercapto methyl sulphonate. Also other suitable isomers of the above listed compounds are known which have similarly low standard redox potentials.

An apparatus is provided, the apparatus configured to determine the concentration of one or more analytes in a fluid sample applied to an electrochemical test device as described herein. The apparatus may comprise circuitry for receiving one or more signals from the electrochemical test device such as an output signal generated from a fluid sample applied to the electrochemical test device. The apparatus may further comprise a memory storing instructions to determine the concentration of the one or more analytes with reference to the received one or more signals. The memory may also store data for the instructions to refer to, for example data mapping the output signal to analyte concentration, or a function of the output signal to be calculated. The apparatus may further comprise a processor configured to perform the instructions stored in the memory.

A method is provided, the method for determining a concentration of a first analyte in a fluid sample and a concentration of a second analyte in the fluid sample, wherein an electrochemical test device is used. The electrochemical test device comprises a set of electrodes comprising a first working electrode, a second working electrode, and a counter/reference electrode. The first working electrode is provided with first sensing chemistry for the first analyte. The first sensing chemistry includes a first electron transfer agent. The second working electrode is provided with second sensing chemistry for the second analyte. The second sensing chemistry includes a second electron transfer agent. The counter/reference electrode is provided with a third electron transfer agent. The first electron transfer agent has a first standard redox potential. The second electron transfer agent has a second standard redox potential. The third electron transfer agent has a third standard redox potential. The third standard redox potential is higher than the second standard redox potential by at least 0.2V. The first standard redox potential is substantially the same as the third redox potential. The method comprises operating in a fuel cell mode for a first period in which the difference between the second standard redox potential and the third standard redox potential causes current to flow from the second working electrode to the counter/reference electrode. The first period serves as a poise delay period for the first working electrode. The method further comprises, after the first time period, applying a potential difference for a second time period between the first working electrode and the counter/reference electrode. The method further comprises determining the concentration of the second analyte based on an output signal generated from the current that flows between the second working electrode and the counter/reference electrode in the first time period. The method further comprises determining the concentration of the first analyte based on an output signal generated from the current that flows between the first working electrode and the counter/reference electrode in the second time period.

While operating a "fuel cell" mode, there may be no potential difference applied to the electrodes—an inherent thermodynamic potential difference may exist between the second working electrode and the counter/reference electrode due to the difference between the third standard redox potential and the second standard redox potential alone. This potential difference may cause current to flow from the second working electrode to the counter/reference electrode, generating an output signal suitable for determining the concentration of the second analyte. While operating in fuel cell mode, the potential difference between the first working electrode and the counter/reference electrode may be 0V, and so no output signal may be generated for determining the concentration of the first analyte. However, while operating in fuel cell mode, the first sensing chemistry on the first working electrode may be, at least in part, reacting with the first analyte in the fluid sample.

Accordingly, there is a poise delay period at the first working electrode leading to an improved output signal for determining the concentration of the first analyte when, after the first period, a potential difference is applied between the first working electrode and the counter/reference electrode.

The third standard redox potential may be greater than the second standard redox potential by at least 0.2V. Preferably, the third standard redox potential is greater than the second standard redox potential by at least 0.3V. More preferably, the third standard redox potential is greater than the second standard redox potential by at least 0.4V.

The first electron transfer agent may be the same as the third electron transfer agent.

The first period may be between 1 and 30 seconds. Optionally, the first period may be between 5 and 20 seconds. Optionally, the first period may be between 15 and 20 seconds. Optionally, the first period may be between 5 and 10 seconds.

Determining the concentration of the second analyte may comprise integrating at least a portion of the output signal.

The potential difference may be between 0.1 and 0.5 Volts. Optionally the potential difference may be between 0.2 and 0.4 Volts. Optionally, the potential difference may be between 0.25 and 0.35 Volts.

The first analyte and the second analyte may be the same analyte. The first sensing chemistry and second sensing chemistry may comprise different enzymes. The first sensing chemistry and second sensing chemistry may comprise the same enzyme.

One of the first and second sensing chemistry may comprise an oxidase. The other of the first and second sensing chemistry may comprise a dehydrogenase. The oxidase may be glucose oxidase and the dehydrogenase may be a flavin adenine dinucleotide (FAD)-dependent glucose dehydrogenase. The oxidase may be glucose oxidase and the dehydrogenase may be a pyrroloquinoline quinone (PQQ)-dependent glucose dehydrogenase.

The sensing chemistry for the first working electrode may comprise potassium ferricyanide. The sensing chemistry for the first working electrode may comprise ruthenium pentaammine pyridine. The sensing chemistry for the second working electrode may comprise ruthenium hexaammine trichloride. The sensing chemistry for the second working electrode may comprise ruthenium pentaammine chloride. The sensing chemistry for the second working electrode may comprise a naphthoquinone derivative such as 1,2 naphthoquinone-4-sulphonate. The sensing chemistry for the second working electrode may comprise 1,4 naphthoquinone-2-mercapto methyl carboxylic acid. The sensing chemistry for the second working electrode may comprise 1,4 naphthoquinone-2-mercapto benzoic acid. The sensing chemistry for the second working electrode may comprise 1,4 naphthoquinone-2-mercapto methyl sulphonate. Also other suitable isomers of the above listed compounds are known which have similarly low standard redox potentials.

The first analyte and the second analyte may be different analytes. The first sensing chemistry and second sensing chemistry may comprise different enzymes. The first sensing chemistry and second sensing chemistry may comprise the same enzyme. The first analyte may be lactate and the second analyte may be glycerol. The first analyte may be lactate and the second analyte may be β-hydroxybutyrate. The first analyte may be lactate and the second analyte may be glucose. The first analyte may be glucose and the second analyte may be glycerol. The first analyte may be glucose and the second analyte may be β-hydroxybutyrate.

For measuring concentrations of lactate and glycerol, or lactate and glucose, or lactate and β-hydroxybutyrate, the first sensing chemistry may comprise potassium ferricyanide and the second sensing chemistry may comprise ruthenium hexaammine trichloride. The first sensing chemistry may comprise potassium ferricyanide and the second sensing chemistry may comprise ruthenium pentaammine chloride. The first sensing chemistry may comprise potassium ferricyanide and the second working electrode may comprise a naphthoquinone derivative such as 1,2 naphthoquinone-4-sulphonate.

For measuring the concentrations of glucose and glycerol, or glucose and β-hydroxybutyrate the first sensing chemistry may comprise potassium ferricyanide and the second sensing chemistry may comprise ruthenium hexaammine trichloride. The first sensing chemistry may comprise potassium ferricyanide and the second sensing chemistry may comprise ruthenium pentaammine chloride. The first sensing chemistry may comprise ruthenium pentaammine pyridine and the second sensing chemistry may comprise ruthenium hexaammine trichloride. The first sensing chemistry may comprise ruthenium pentaammine pyridine and the second sensing chemistry may comprise ruthenium pentaammine chloride.

One of the first and second sensing chemistry may comprise an oxidase and the other of the first and the second sensing chemistry may comprise a dehydrogenase.

An apparatus is disclosed for determining a concentration of a first analyte in a fluid sample and a concentration of a second analyte in the fluid sample. The apparatus comprises circuitry for receiving an output signal generated from the fluid sample. The apparatus further comprises a memory storing instructions to perform a method as disclosed herein. The memory may also store data for the instructions to refer to, for example data mapping the output signal to analyte concentration, or a function of the output signal to be calculated. The apparatus further comprises a processor configured to perform the instructions stored in the memory.

A machine-readable medium is disclosed, the machine-readable medium having instructions stored thereon. The instructions are configured such that when read by a machine the instructions cause a method as disclosed herein to be carried out.

An electrochemical test device for use in determining a concentration of a first analyte in a fluid sample and a concentration of a second analyte in the fluid sample is disclosed. The device comprises a set of electrodes comprising a first working electrode, a second working electrode and a counter/reference electrode. The first working electrode is provided with first sensing chemistry for the first analyte. The first sensing chemistry includes a first electron transfer agent. The second working electrode is provided with second sensing chemistry for the second analyte. The second sensing chemistry includes a second electron transfer agent. The counter/reference electrode is provided with a third electron transfer agent. The first electron transfer agent has a first standard redox potential and the second electron transfer agent has a second standard redox potential and the third electron transfer agent has a third standard redox potential. The third standard redox potential is higher than the second standard redox potential by at least 0.2V. The first standard redox potential is substantially the same as the third standard redox potential. "Substantially the same" in the context of these electron transfer agents means having a standard redox potential which is within 0.1V of each other.

The first electron transfer agent may be the same as the third electron transfer agent.

Preferably, the third standard redox potential is greater than the second standard redox potential by at least 0.3V. More preferably, the third standard redox potential is greater than the second standard redox potential by at least 0.4V.

The first analyte and the second analyte may be the same analyte. The first sensing chemistry and second sensing chemistry may comprise different enzymes. The first sensing chemistry and the second chemistry may comprise the same enzymes. The first analyte and second analyte may be glucose.

One of the first and second sensing chemistry may comprise an oxidase and the other of the first and second sensing chemistry may comprise a dehydrogenase. The oxidase may be glucose oxidase and the dehydrogenase may be a flavin adenine dinucleotide (FAD)-dependent glucose dehydrogenase. The oxidase may be glucose oxidase and the dehydrogenase may be a pyrroloquinoline quinone (PQQ)-dependent glucose dehydrogenase.

The first analyte and the second analyte may be different analytes. The first sensing chemistry and second sensing chemistry may comprise different enzymes. The first sensing chemistry and the second chemistry may comprise the same enzymes. The first analyte may be lactate and the second analyte may be glycerol. The first analyte may be lactate and second analyte may be β-hydroxybutyrate. The first analyte may be lactate and the second analyte may be glucose. The first analyte may be glucose and the second analyte may be glycerol. The first analyte may be glucose and the second analyte may be β-hydroxybutyrate. One of the first and second sensing chemistry may comprise an oxidase and the other of the first and second sensing chemistry may comprise a dehydrogenase. The oxidase may be glucose oxidase and the dehydrogenase may be a flavin adenine dinucleotide (FAD)-dependent glucose dehydrogenase. The oxidase may be glucose oxidase and the dehydrogenase may be a pyrroloquinoline quinone (PQQ)-dependent glucose dehydrogenase.

The sensing chemistry for each of the first and second working electrodes may be disposed in at least one layer.

FIG. 1 shows an apparatus in the form of a test strip-meter system 10. System 10 comprises a meter 12 for receiving an output signal from an electrochemical test device such as electrochemical test strip 14. Electrochemical test strip 14 comprises a set of electrodes which typically comprises one or more working electrodes (not shown in FIG. 1) and a counter/reference electrode, each of the working electrodes provided with sensing chemistry for reacting with at least one analyte of a fluid sample to be applied to electrochemical test strip 14. In this example, each of the one or more working electrodes has reagents coated thereon. The counter/reference electrode may also have reagents coated thereon. Meter 12 comprises receiving means 13 for receiving electrochemical test strip 14 and applying a potential difference to the working electrode(s) and the counter/reference electrode.

Meter 12 further comprises processing circuitry 15 for carrying out various functions relating to the operation of meter 12. For example, processing circuitry 15 is configured to control operation of receiving means 13 so as to control application of a potential difference between the working electrode(s) and the counter/reference electrode. Processing circuitry 15 is further configured to process one or more output signals generated at test strip 14 and to control a display of messages on display 18. The processing circuitry may perform other functions. Meter 12 further comprises first and second memory storages 16a and 16b. Although two memory storages are shown, in other embodiments the memory storages may be combined to form a single memory storage, or meter 12 may comprise more than two memory storages. Meter 12 also comprises a display 18 for displaying readouts of measurements taken by meter 12.

When manufacturing an electrochemical test device such as electrochemical test strip 14 the device can be constructed in layers with different layers providing different features such as conductive tracks, electrode area definition and positioning of chemistry. Suitable manufacturing techniques may be used such as deposition techniques (e.g. printing such as thick-film printing methods including screen printing, rotary printing, serigraph printing, gravure printing and sub-microlitre controlled volume drop on demand printing technologies) and adherence of layers, as will be apparent from the following.

Figure 2:
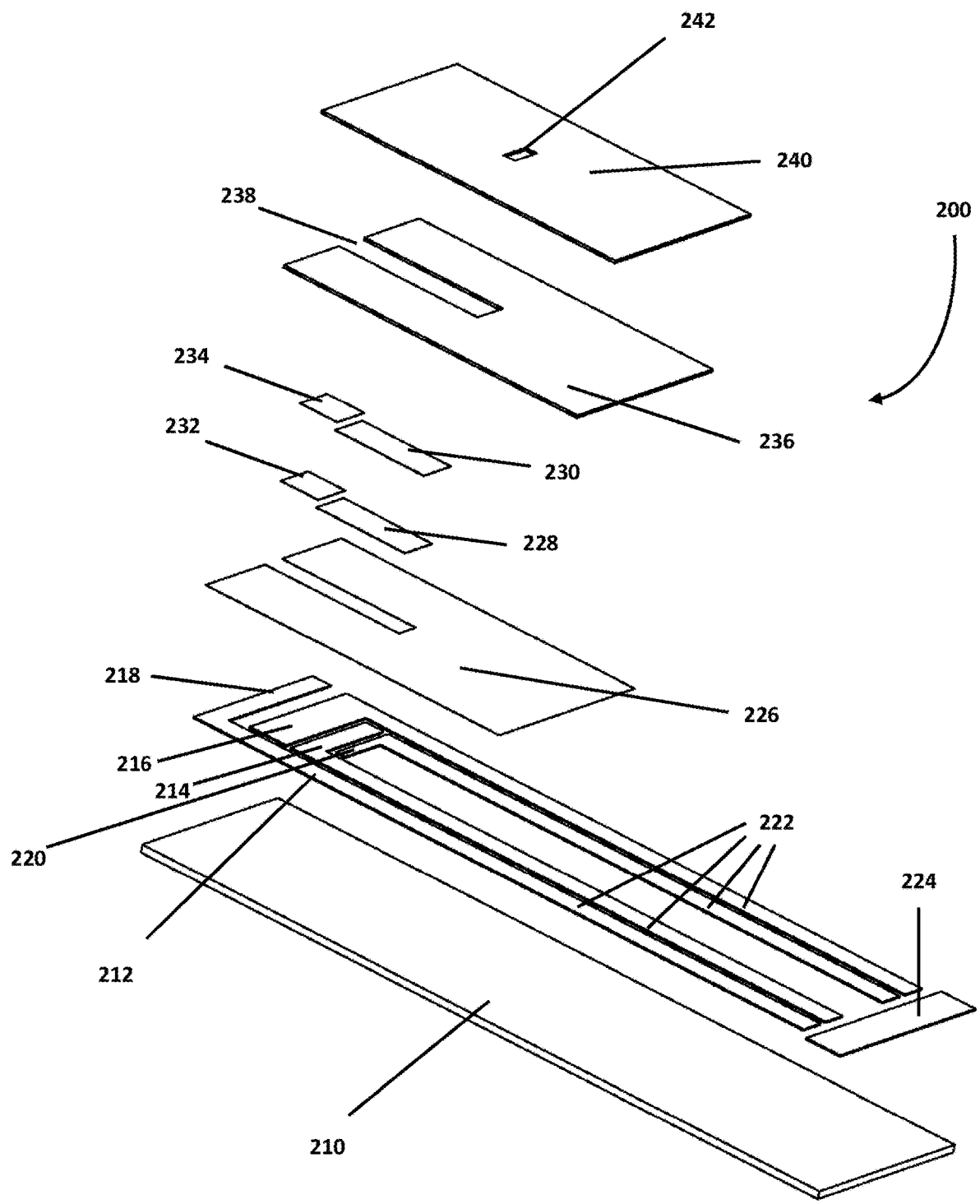
FIG. 2 shows an exploded view of an electrochemical test device.

FIG. 2 shows a perspective, exploded view of an electrochemical test device in the form of electrochemical test strip 200 according to a first example. This example will be described in relation to a received blood sample of around 0.5 μl in volume, although the electrochemical test strip 200 could be used with any suitable fluid sample. The electrochemical test strip 200 shown in FIG. 2 has an end-fill configuration i.e. the blood sample can be received at one end of the electrochemical test device 200.

The electrochemical test strip 200 comprises a support layer or substrate 210. Substrate 210 has a thickness of around 0.35 mm. The substrate 210, in this example, is made from polyester, although any suitable substrate may be used. The substrate 210 is thermally and dimensionally stable, with consistent properties such as thickness, surface roughness and surface energy.

Above the substrate 210 is the conductor layer 212. In this example, the conductor layer 212 is directly disposed upon the substrate 210 using carbon-based ink. In this example, the conductor layer 212 is printed directly onto the upper surface of the substrate 210. The conductor layer 212 may be printed onto the substrate 210 using screen printing, lithographic printing, tomographic printing, sub-microlitre controlled volume drop on demand printing technologies, or any other suitable method of printing. The conductor layer comprises a set of electrodes including a first working electrode 214, counter/reference electrode 216, a second working electrode 218 and fill-sufficiency detect electrode 220. The conductor layer 212 further comprises a set of conductive tracks 222. In this example, the conductive tracks 222 extend along the longitudinal axis of the electrochemical test strip 200. The conductive tracks are suitable for electrically coupling the electrodes to a meter 12. The conductor layer 212 further comprises a switch-on bar 224 for activating a meter 12.

Above the conductor layer 212 is an insulator layer 226. The insulator layer 226 is made of an electrically insulating material, and is directly disposed upon the upper surface of the conductor layer 212. The insulator layer 226 is, in this example, made of a dielectric material and defines an interaction area. That is, the insulation layer 226 electrically insulates some portions of the conductor layer 212 from the layers situated above in the electrochemical test strip 200. Specially designed gaps in the insulator layer 226 expose some portions of the conductor layer 212 to the layers situated above in the electrochemical test strip 200. In this way, the insulator layer 226 defines which part or parts of the electrodes of the conductor layer 212 are able to come into contact with an applied blood sample for the measurement of the analyte.

Sensing chemistry is applied to the electrodes of the conductor layer 212. In this example, the sensing chemistry comprises four reagent layers 228, 230, 232 and 234 which are applied to exposed electrode interaction areas after the insulator layer 226 is formed. More or fewer reagent layers may be present. A first reagent layer 228 is applied to both the first working electrode 214 and the counter/reference electrode 216. In this example, the first reagent layer 228 is also applied to the fill-sufficiency detect electrode 220. An additional analyte-sensitive layer 230 is applied to the first working electrode 214, the counter/reference electrode 216 and the fill-sufficiency detect electrode 220. In this way, the first working electrode 214 is provided with sensing chemistry for a first analyte. The sensing chemistry for the first working electrode 214 comprises suitable reagents for detecting the first analyte. As the reagent layers (228, 230) for the first working electrode 214 and the counter/reference electrode 216 are the same, the potential difference between the first working electrode 214 and the counter/reference electrode 216 is substantially 0V when the electrochemical test strip 200 is not in use i.e. when no potential difference is applied to the electrodes or when no sample has been applied to the test strip.

The second working electrode 218 has sensing chemistry (reagent layers 232 and 234) for a second analyte. In particular, the sensing chemistry for the second analyte comprises a diaphorase, an electron transfer agent, an NAD(P)$^+$-dependent dehydrogenase and a cofactor for the NAD(P)$^+$-dependent dehydrogenase. Depending on the electron transfer agent provided at the second working electrode 218, the potential difference between the second working electrode 218 and the counter/reference electrode 216 may be substantially 0 V or may be non-zero.

Above the insulator layer 226 is a spacer layer 236 formed of a polyester core. The spacer layer 236 defines a sample introduction channel 238, or measurement chamber, for introducing a blood sample to the conductor layer 212. The height of the sample introduction channel 238 is defined by the thickness of the spacer layer 236. The spacer layer 236 is formed of double sided adhesive tape which, in this example, is applied directly to the upper surface of the insulator layer 226. The sample introduction channel 238 is formed by providing a gap into the double sided adhesive tape of the spacer layer 236. The thickness of the spacer layer 236 is approximately 0.1 mm, which provides a good balance between the volume of the sample introduction channel 238 and the performance of the electrochemical test strip 200.

Above the spacer layer 236 is a cover layer 240. During manufacture, the spacer layer 236 and the cover layer 240 may be applied to the test strip 200 separately or as a single prelaminated layer, although in this example the cover layer 240 is a separate layer to the spacer layer 236. The cover layer 240 acts as a ceiling to the sample introduction channel 238, thereby substantially closing the sample introduction channel 238 from above. The cover layer 240 is formed of single sided tape and, in this example, is adhered directly to the upper surface of the spacer layer 236. The lower surface of the cover layer 240 has hydrophilic properties, which assist in drawing a blood sample into the sample introduction channel 238. The cover layer 240 further has a vent 242 suitable for venting air out of the sample introduction channel 238 to allow a blood sample to enter the sample introduction channel 238 via capillary action. The vent 242 is narrower than the sample introduction channel 238 so that air may easily vent from the sample introduction channel 238 but blood or any other fluid will not easily be able to pass through the vent 242.

In use, a fluid sample is provided to the electrochemical test device and a potential difference may be applied across the fluid sample to generate a detectable output signal indicative of one or more analyte concentrations in the fluid sample. In this example, in use a blood sample is applied to the sample introduction channel 238 of the electrochemical test strip 200. Through capillary action, the blood is drawn into the sample introduction channel 238 to the electrodes 218, 216 and 214 of the conductor layer 212. That is, the sample introduction channel 238 acts as a capillary channel. If the electron transfer agent on the second working electrode 218 is different from the electron transfer agent on the counter/reference electrode 216 then an inherent thermodynamic potential difference may exist that is large enough to cause a current to flow between the counter/reference electrode 216 and the second working electrode 218 when the second analyte is present in the blood sample. This current may be used to measure a concentration of the second analyte in the blood sample without the requirement to apply a further potential difference across the electrodes. If, as in this example, the electron transfer agent applied to the counter/reference electrode 216 and the first working electrode 214 is the same then the inherent thermodynamic potential difference between the counter/reference electrode 216 and the first working electrode 214 may be approximately 0V. If a potential difference is then applied across the first working electrode 214 and the counter/reference electrode 216 then a current may be produced from the fluid sample based on a concentration of the first analyte in the fluid sample. In this way, concentrations of the first and second analyte may be measured. The first analyte and the second analyte may or may not be the same.

Figure 3:
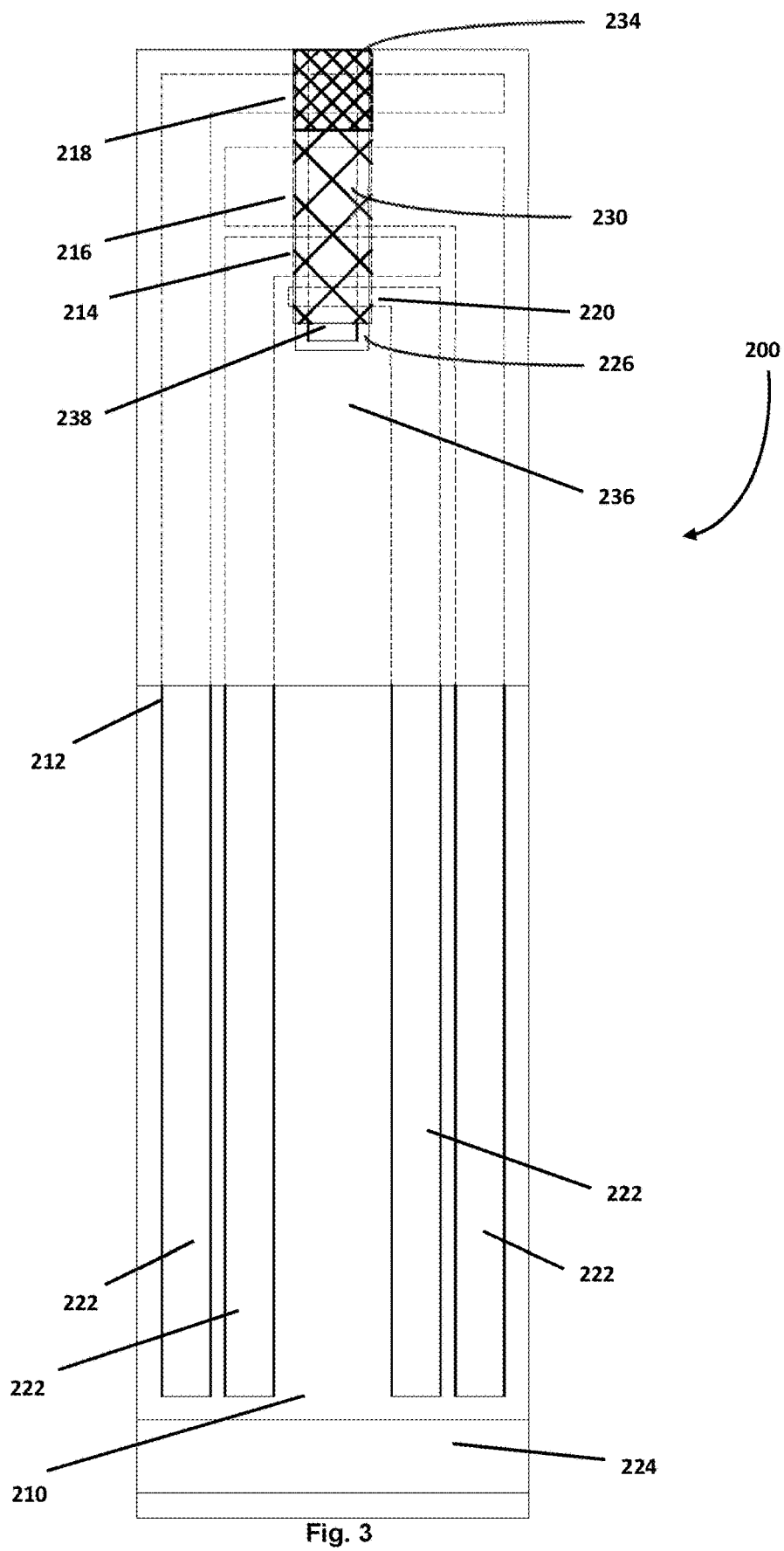
FIG. 3 shows a plan view of some layers of an electrochemical test device.

FIG. 3 depicts a plan view of some of the layers of the electrochemical test strip 200 of FIG. 2. In particular, FIG. 3 shows the substrate 210, the conductor layer 212, the insulator layer 226, the reagent layers 230, 234 (reagent layers 228, 232 below are not visible), and the spacer layer 236. The cover layer 240 is not shown in FIG. 3 for clarity. The respective reagent layers are applied to the exposed areas of each of the working electrodes 214 and 218, the counter/reference electrode 216 and the fill-sufficiency detect electrode 220.

In the electrochemical test device 200 of FIG. 3, the reagent layers 228 and 230 applied to the counter/reference electrode 216, first working electrode 214 and fill-sufficiency detect electrode 220 are shown to be touching the reagent layers 232 and 234 applied to the second working electrode 218. There may be a gap between the sensing chemistry of the counter/reference electrode 216 and the sensing chemistry of the second working electrode 218. The sensing chemistry layers may touch. Preferably only one electron transfer agent extends over the counter/reference electrode.

Figure 4:
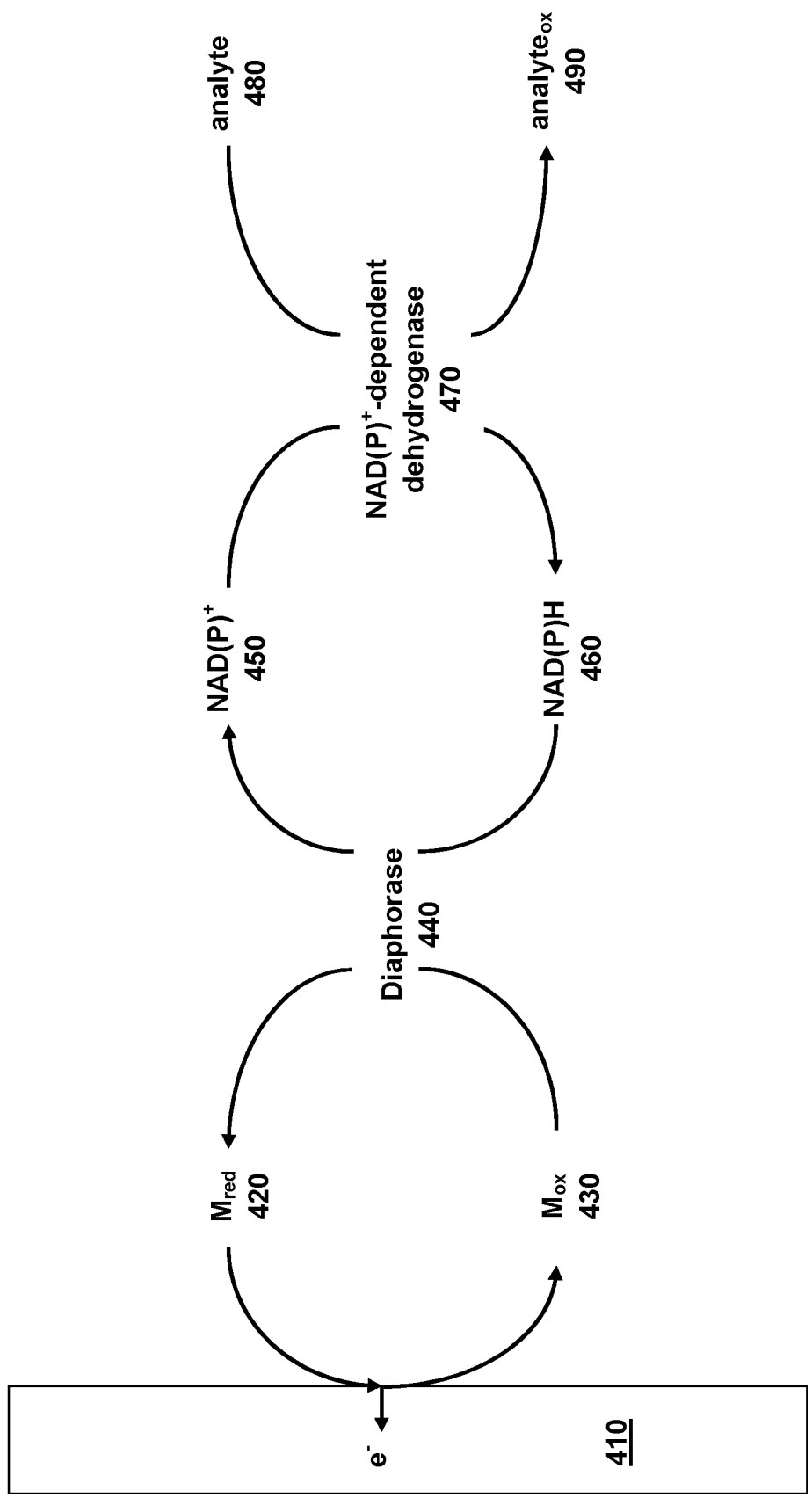
FIG. 4 illustrates bio-electrocatalysis at an electrode.

FIG. 4 is an illustration of bio-electrocatalysis at an electrode 410, which may correspond to second working electrode 218 above, according to an example. In this example, electrode 410 is coated with layers of sensing chemistry suitable for reacting with an analyte 480 in a fluid sample. The sensing chemistry comprises a cofactor NAD(P)$^+$ 450, a NAD(P)$^+$-dependent dehydrogenase 470 for reacting with the analyte 480, a diaphorase 440 and an electron transfer agent or mediator (its reduced form $M_{red}$ 420 and its oxidised form $M_{ox}$ 430).

The diaphorase 440 and the entrapped mediator (420, 430) carry out the following reactions:

(2)

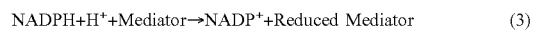
(3)

Either NADH or NADPH may be used as reductants.

With reference to FIG. 4, when in the presence of a fluid sample, a cofactor NAD(P)$^+$ 450 and a potential difference between the electrode 410 and a counter/reference electrode, an NAD(P)$^+$-dependent dehydrogenase 470 interacts with the analyte 480 of the fluid sample. NAD(P)H 460 is produced as a result of the interaction, as is an oxidised form of the analyte 490. In the presence of a diaphorase 440 (which acts as a catalyst), an oxidised form of a mediator 430 reacts with the NAD(P)H 460 at the active site of the diaphorase 440 to produce a reduced mediator 420 and NAD(P)$^+$ 450. The reduced form of the mediator 420 then transfers electrons (e$^-$) to the electrode 410. In this way, the sensing chemistry applied to electrode 410 accomplishes the transfer of electrons from the fluid sample to the conducting electrode 410. A signal is thus generated to be detected by a strip meter.

Figure 5:
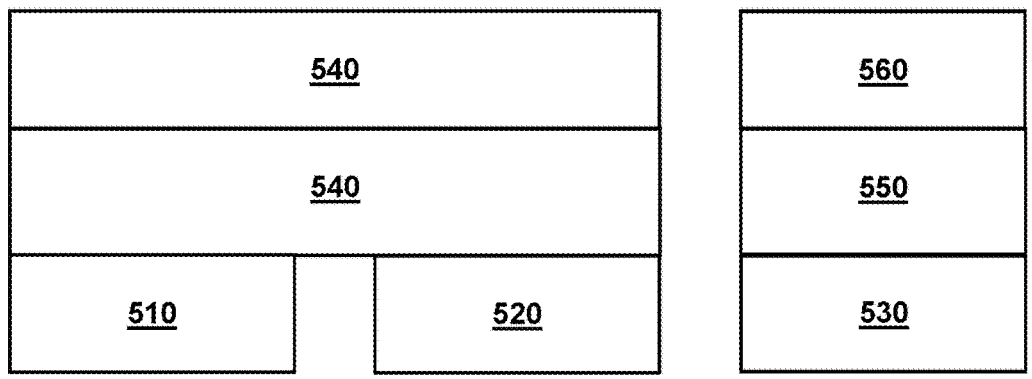
FIG. 5 shows reagent layers that may be applied to two working electrodes.

FIG. 5 is a schematic showing the respective reagent layers applied to the electrodes of an electrochemical test device according to an example. In FIG. 5, a first working electrode 510, a counter/reference electrode 520, and a second working electrode 530 are shown. The first working electrode 510 may correspond to the first working electrode 214 of FIG. 2. Similarly, the counter/reference electrode 520 and the second working electrode 530 may respectively correspond to the counter/reference electrode 216 and the second working electrode 218 of FIG. 2. In this example, the first working electrode 510 and the counter/reference electrode 520 are coated in two layers 540 of reagents. In particular, the reagent layers 540 comprise an electron transfer agent and a suitable reagent for reacting with a first analyte in the sample. The second working electrode 530 is provided with two layers of sensing chemistry 550, 560. The layer 550 adjacent the second working electrode 530 comprises a diaphorase and an electron transfer agent. Reagent layer 560 comprises an NAD(P)$^+$-dependent dehydrogenase for reacting with a second analyte in the sample and a cofactor for the NAD(P)$^+$-dependent dehydrogenase.

Additionally, each layer of the sensing chemistry comprises suitable buffers, surfactants and other additives. For example, the sensing chemistry may comprise one or more of a buffer, a gelling or thickening agent such as hydroxyethyl cellulose (HEC) or other cellulosic polymers, a rheology/viscosity modifier such as silica, flavin mononucleotide (FMN) for stabilising the diaphorase and a surfactant such as Tween 20.

In a specific example, in an electrochemical test device for measuring a concentration of lactate and a concentration of glycerol in a fluid sample, the sensing chemistry may be applied in layers as in FIG. 5. In this example, the electron transfer agent in the layers 540 coating the first working electrode 510 and the counter/reference electrode 520 is a ferricyanide anion such as potassium ferricyanide which has a standard redox potential of approximately 0.44V. Reagent layers 540 further comprise lactate oxidase for reacting with lactate in the fluid sample. The electron transfer agent provided in layer 550 on the second working electrode is ruthenium hexaammine trichloride which has a standard redox potential of approximately 0.1V. The NAD(P)$^+$-dependent dehydrogenase and cofactor in layer 550 are glycerol dehydrogenase and NAD$^+$ respectively.

Potassium ferricyanide has a number of benefits as a mediator. In particular, potassium ferricyanide is highly water soluble, has a small molecular weight and fast homogeneous and heterogeneous kinetics. Accordingly potassium ferricyanide supports a large analyte measurement range. Although potassium ferricyanide has been used as the mediator in this example, any suitable mediator may be used.

Ruthenium hexaammine trichloride has a standard redox potential of approximately 0.1 Volts, which corresponds to an overpotential with respect to the NAD(P)$^+$/NAD(P)H redox couple of approximately 0.415 Volts. Accordingly, ruthenium hexaammine trichloride is a good candidate for use in an electrode for measuring glycerol, for which the sensitivity of the electrochemical test device is an issue. Additionally, ruthenium hexaammine trichloride does not react with surface amino acids in the diaphorase which could lead to a deterioration in electrode performance. In addition it is known that this molecule is stable over time, reacting little to, for example, moisture, sunlight, temperatures experienced during manufacture and conditions experienced in storage. Accordingly, the sensitivity of an electrochemical test device incorporating this mediator will not deteriorate rapidly over time.

On receiving a fluid sample, such as a blood sample, at first no potential difference is applied across the electrodes. As the mediator, potassium ferricyanide, on the first working electrode 510 and the counter/reference electrode 520 is the same, these two electrodes will be substantially at equilibrium and so no current will flow between the first working electrode 510 and the counter/reference electrode 520. The potential difference between the working electrodes and the counter/reference electrode 520 is maintained at 0V. As the ruthenium hexaammine trichloride mediator on the second working electrode has a lower standard redox potential than the potassium ferricyanide mediator on the counter/reference electrode 520, there is an inherent thermodynamic potential difference of approximately 0.34V which allows current to flow between the second working electrode 530 and the counter/reference electrode 520 allowing any reduced mediator species formed due to the biochemical reaction (of glycerol in the fluid sample with glycerol dehydrogenase in layer 560) to be oxidised. The current signal can be interrogated by a test meter and can be used to derive analytical data from the second working electrode 530. In this way, the concentration of glycerol in the sample can be measured or inferred from measurement, even when no additional potential difference is applied to the electrodes of the electrochemical test device.

During the time period at which the fluid sample is present but no additional potential difference is applied to the electrodes of the electrochemical test device, there is no flow of current between the first working electrode 510 (configured in this example for detecting lactate) and the counter/reference electrode 520. However, during this period, the concentration of potassium ferrocyanide accumulates due to the lactate concentration-dependent activity of the lactate oxidase. Subsequently, a voltage of approximately 0.3 V is applied across the first working electrode 510 and the counter/reference electrode 520 allowing current to flow between the first working electrode 510 and counter/reference electrode 520, and the concentration of ferrocyanide is detected amperometrically. Accordingly, the concentrations of both glycerol and lactate in the fluid sample can be measured.

Figure 6:
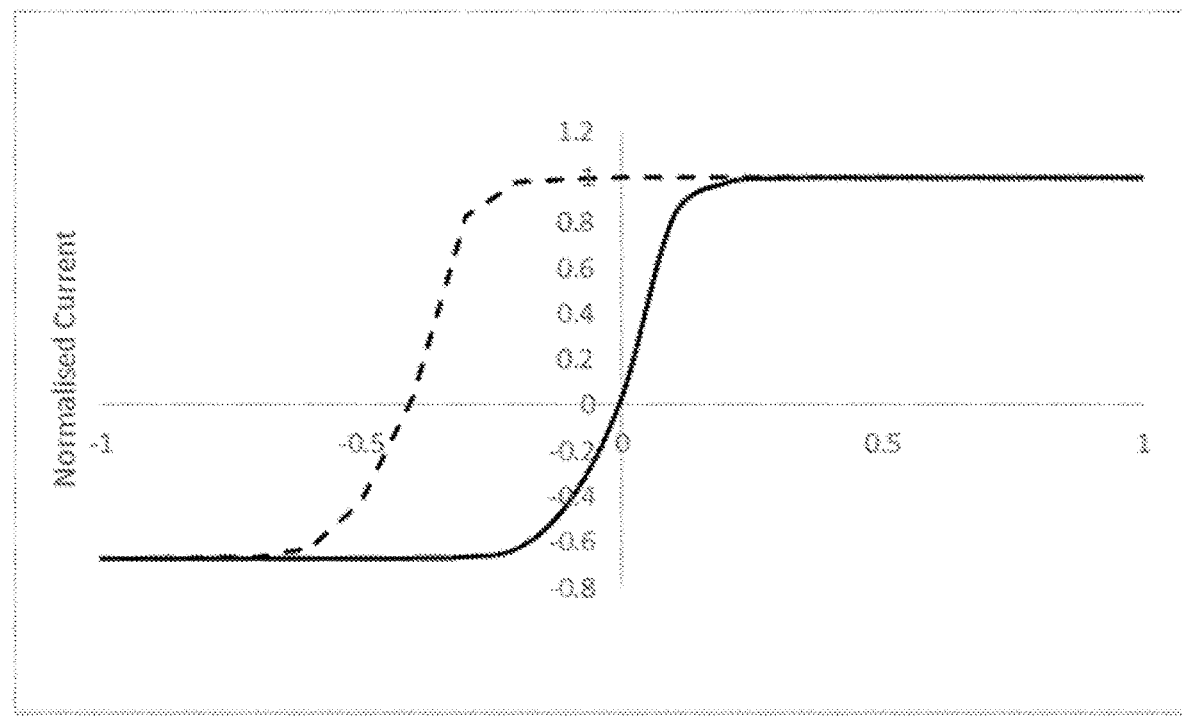
FIG. 6 shows polarisation curves for two working electrodes provided with different electron transfer agents which have different redox potentials.

FIG. 6 shows representative polarisation curves for a lactate sensitive electrode provided with potassium ferricyanide (solid curve) and a glycerol sensitive electrode provided with a ruthenium based electron transfer agent (dashed curve). The potential difference is expressed relative to the potassium ferricyanide/ferrocyanide counter/reference electrode 520. At a potential difference of 0V, there is no current flow from the potassium ferricyanide based chemistry of the first working electrode (solid curve) whereas the ruthenium based chemistry (dashed curve) is already at a diffusion limited plateau. Due to the differences in the magnitude of response from the two electrodes the currents have been normalised. Data was collected using artificial plasma spiked with lactate (1 mM) and glycerol (1 mM).

Figure 7:
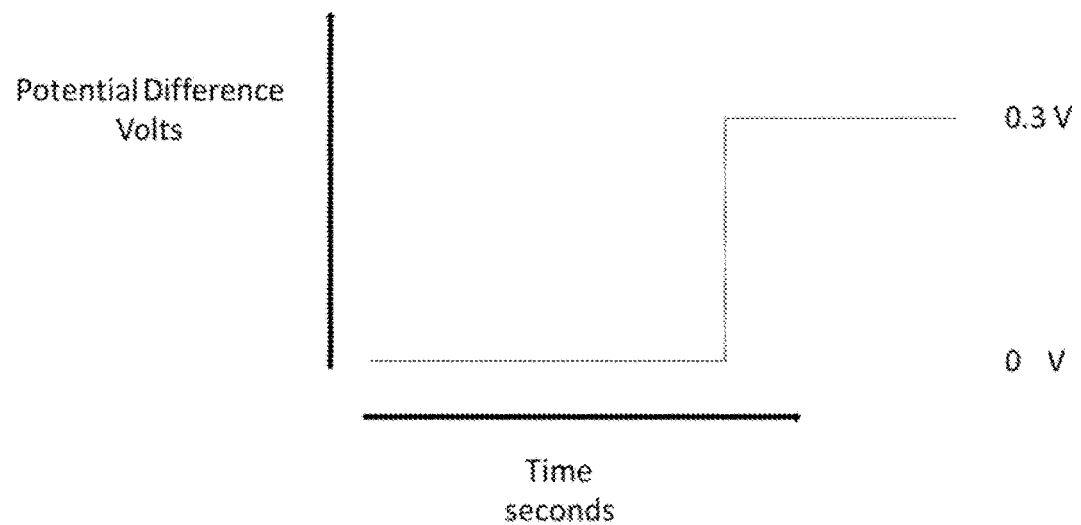
FIG. 7 shows an example waveform applied by a meter.

FIG. 7 shows an example waveform applied to the test strip by the meter that can be used in order to measure the concentrations of lactate and glycerol. The wave form comprises two segments. During the first segment, the potential difference between the first working electrode 510 and the counter/reference electrode 520 is maintained at 0 V. As the mediator on the second working electrode is different from the mediator on the counter/reference electrode 520, detection of glycerol can occur as described above. Also during the first segment, the reaction of the lactate oxidase at the first working electrode 510 with lactate in the fluid sample leads to an increase in the concentration of potassium ferrocyanide. During the second segment a potential difference is applied, in this example 0.3V and the concentration of lactate in the fluid sample is measured.

Figure 8:
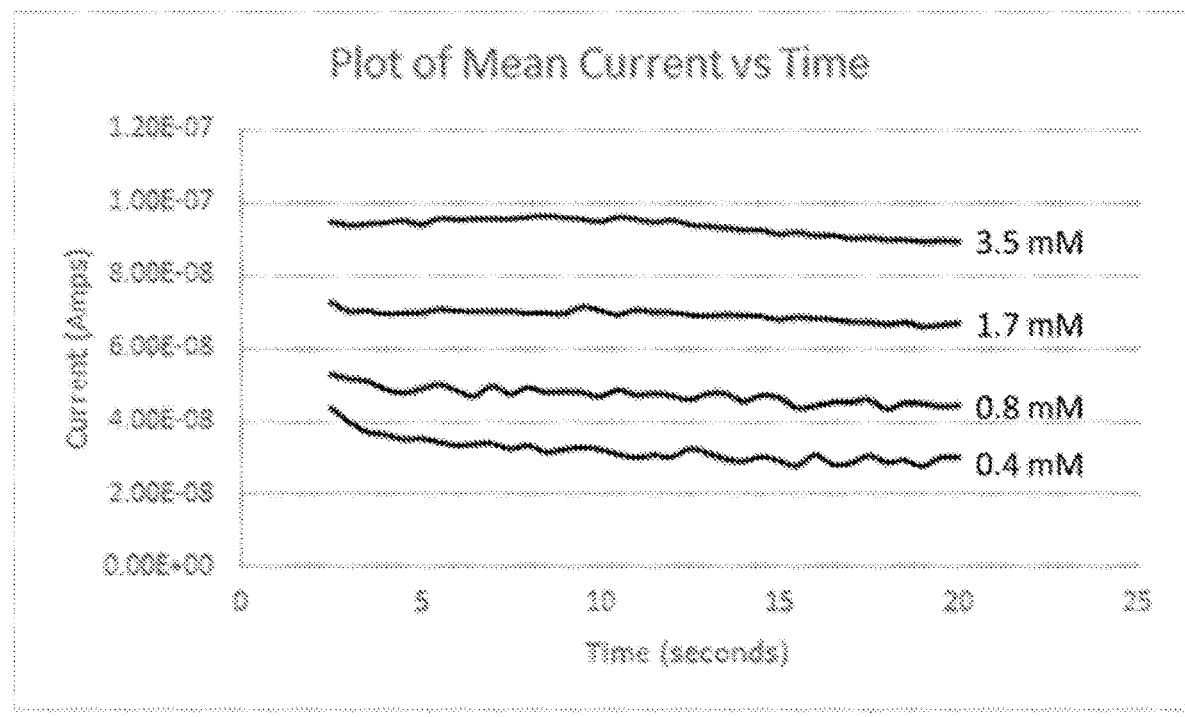
FIG. 8 is a graph of current against time for samples having varying glycerol concentrations.

FIG. 8 shows the output for four different concentrations of glycerol from a test strip such as that discussed above in relation to FIG. 5, during a time period for which the potential difference applied to the electrodes is 0V. To obtain the data in FIG. 8, the potential difference was maintained at 0V for a period of 20 seconds prior to the application of a 0.3V potential step during which a lactate measurement may be made. Data was collected using artificial plasma spiked with varying concentrations of glycerol. The data in FIG. 8 demonstrates that there is a correlation between the current during this measurement phase and the concentration of glycerol in a fluid sample.

Figure 9:
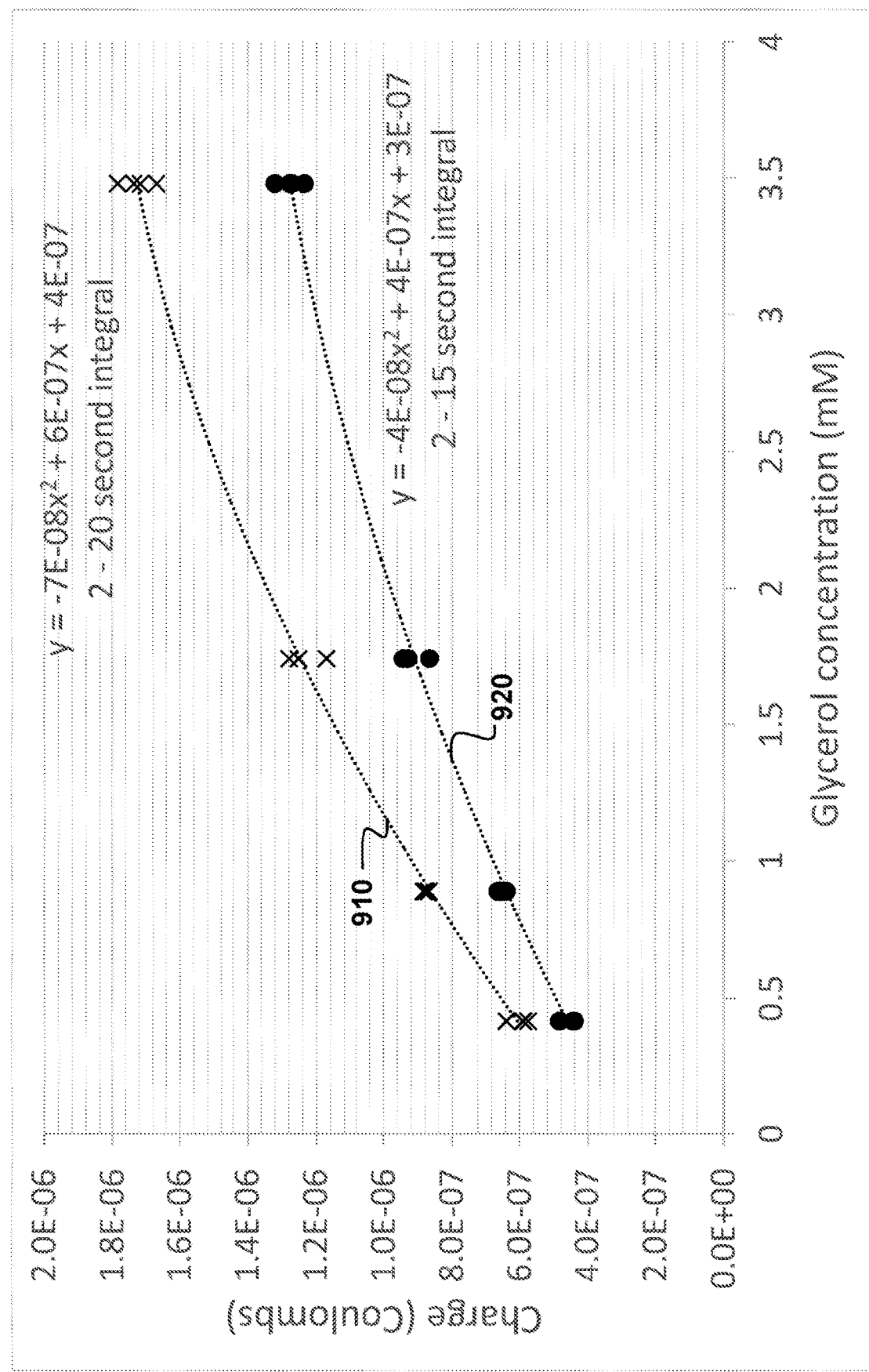
FIG. 9 shows a graph of charge against glycerol concentration for different integral periods.

As the glycerol detection chemistry has relatively slow kinetics (due to the low activity of glycerol dehydrogenase, 40 u/mg and an unfavourable equilibrium constant at pH values below 11) and as the glycerol concentration is usually low in a fluid sample, the current generated by the electrochemical test device is low. In order to improve the signal and hence the sensitivity of the electrochemical test device it can be advantageous to summate the current values during the measurement phase The result of integrating the current over the time points 2-20 seconds (dashed curve 910) or 2-15 seconds (dashed curve 920) is illustrated in FIG. 9. In FIG. 9, the output currents from the individual sensors are plotted as a function of glycerol concentration. FIG. 9 illustrates how the sensitivity of the measurement can be increased by increasing the length of the integral. For example, increasing the integration period to 2-20 seconds from 2-15 seconds results in approximately a 15% increase in sensitivity.

Figure 10:
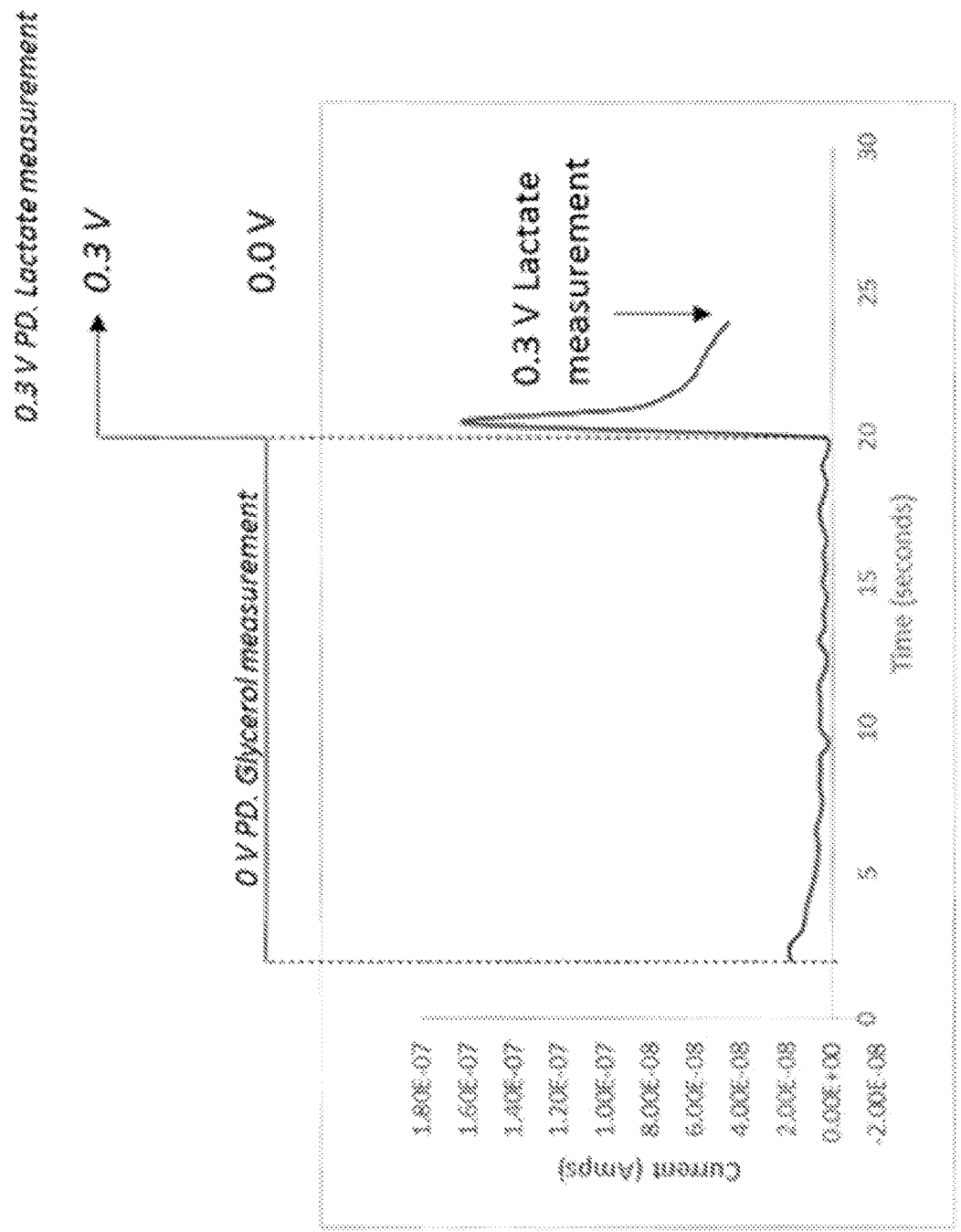
FIG. 10 shows a representative current against time for a glycerol/lactate electrochemical test device.

FIG. 10 is a composite plot showing analytical aspects of both working electrodes. At 0-20 s the current signal output from the second working electrode is shown. At 20-23 s the current signal output from the first working electrode is shown. The proposed meter waveform is also shown. Glycerol concentration is measured over the time period 0-20 seconds. After this time the potential difference across the first working electrode 510 and the counter/reference electrode 520 is increased to 0.3V relative to the counter/reference electrode 520 and only the first working electrode 510 is interrogated.

Figure 11:
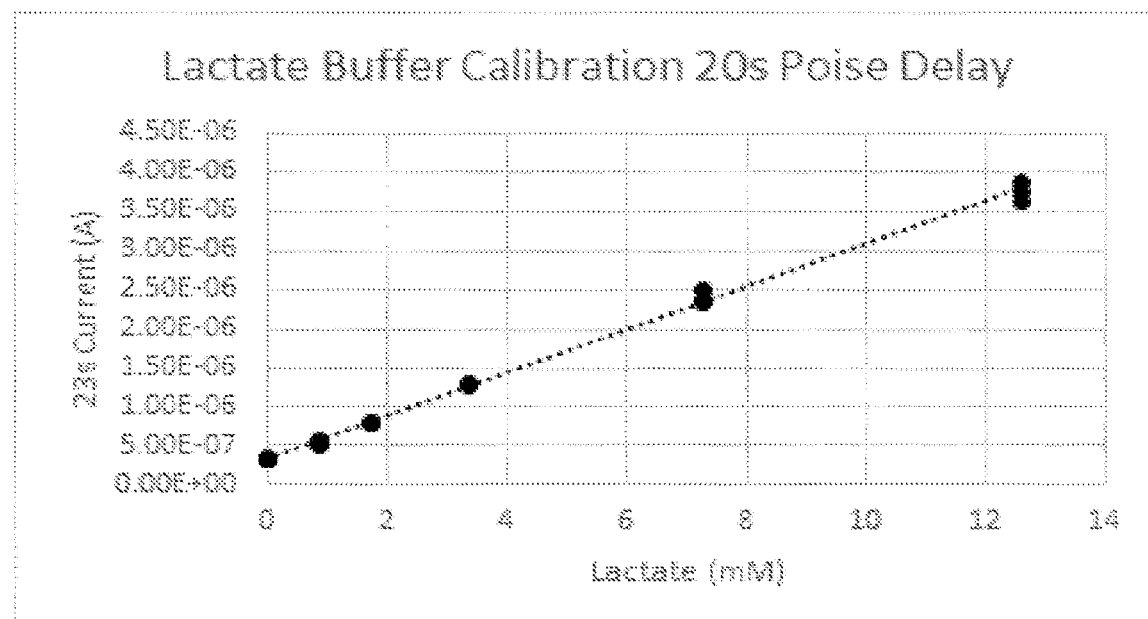
FIG. 11 shows a graph of the dose response curve for lactate.

FIG. 11 shows the dose response curve for lactate over the range 0-12.5 mM after the 20 s poise delay as a result of operating the electrochemical device in fuel cell mode. The 23 s current value was used as the measurand for the lactate.

In another specific example, in an electrochemical test device for measuring a concentration of lactate and a concentration of β-hydroxybutyrate, the sensing chemistry may be applied in layers as in FIG. 5. In this example, the sensing chemistry 540 for the first working electrode 510 and the counter/reference electrode 520 is lactate oxidase. The electron transfer agent in the layers 540 coating the first working electrode 510 and the counter/reference electrode 520 is a ferricyanide anion such as potassium ferricyanide. The electron transfer agent provided in layer 550 on the second working electrode is ruthenium hexaammine trichloride. The NAD(P)$^+$-dependent dehydrogenase and cofactor in layer 550 are β-hydroxybutyrate dehydrogenase and NAD' respectively.

As described above in relation to the previous example, on receiving a fluid, such as a blood sample, no potential difference is applied across the electrodes. As the mediator on the first working electrode 510 and the counter/reference electrode 520 is the same, these two electrodes will be substantially at equilibrium and so no current will flow between the first working electrode 510 and the counter/reference electrode 520. The applied potential difference between the working electrodes and the counter/reference electrode 520 is maintained at substantially 0V. As the ruthenium hexaammine trichloride mediator on the second working electrode has a lower standard redox potential than the potassium ferricyanide mediator on the counter/reference electrode 520, there is an inherent thermodynamic potential difference of approximately 0.34V which allows current to flow between the second working electrode 530 and the counter/reference electrode 520 allowing any reduced mediator species formed due to the biochemical reaction (of β-hydroxybutyrate in the fluid sample with β-hydroxybutyrate dehydrogenase in layer 560) to be oxidised. The current flow can be interrogated by a test meter and can be used to derive analytical data from the second working electrode 530. In this way, the concentration of β-hydroxybutyrate in the sample can be calculated, even when no potential difference is externally applied to the electrodes of the electrochemical test device. Once a suitable potential difference is applied to the first working electrode 510 and the counter/reference electrode 520, the concentration of lactate in the sample can be measured as described previously.

Figure 12:
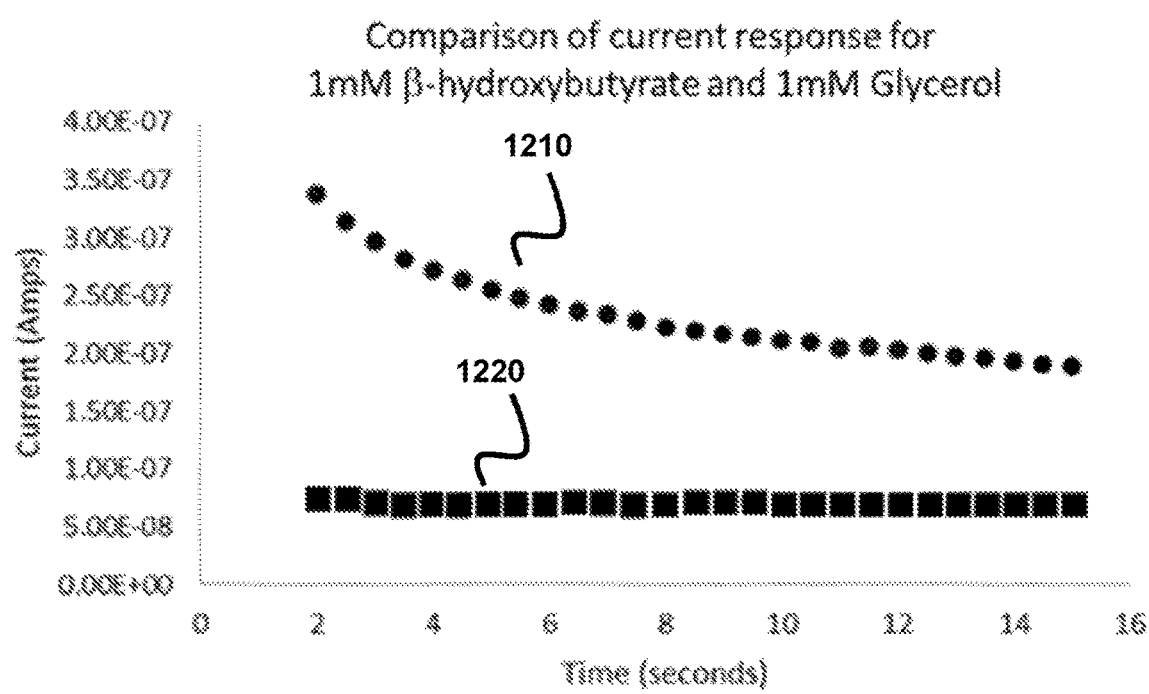
FIG. 12 shows a comparison of current against time for a blood β-hydroxybutyrate and glycerol.

FIG. 12 shows the current against time response (for the time period of 2-15 seconds from when the sample is introduced to the electrodes) during the 0 V applied potential difference phase for the detection of 1 mM β-hydroxybutyrate and 1 mM glycerol in a lactate/6-hydroxybutyrate and a lactate/glycerol test strip respectively. As can be seen, for equivalent concentrations the current generated by the β-hydroxybutyrate chemistry 1210 is greater than that generated by the glycerol chemistry 1220. For example, at 15 seconds the current for the glycerol chemistry is approximately 68 nA compared to approximately 190 nA for the β-hydroxybutyrate chemistry. This is principally due to the better kinetics of the β-hydroxybutyrate formulation driven principally by the higher specific activity of the β-hydroxybutyrate dehydrogenase (2,210 U/mg) and a favourable equilibrium constant. Consequently, a different form of integration can be used for the β-hydroxybutyrate measurement. For example, a single current measurement after 5 seconds can be used. An integral over a shorter time window such as 2-5 seconds may be used. As described even though the glycerol and β-hydroxybutyrate sensor characteristics are different, the same measurement strategy can still be employed.

Blood was collected from two donors post exercising. Donor 1 had undergone a low intensity exercise whereas Donor 2 had undergone a high intensity exercise regime. Plasma values of lactate and glycerol for Donor 1 and Donor 2 post exercise were measured on a YSI 2300 and a Randox Monza Analyser respectively. The reference values are summarised in the table of FIG. 13.

Figures 13, 14:
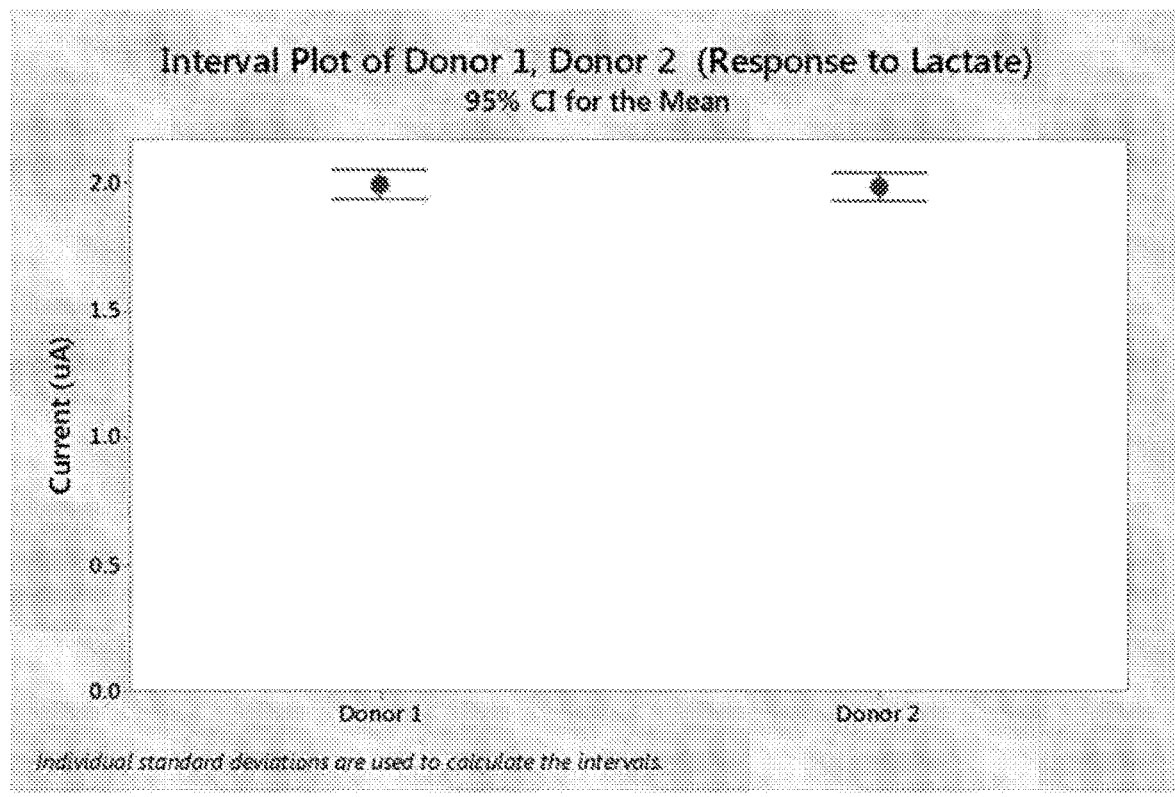
FIG. 13 is a table of glycerol and lactate reference values for whole blood measurements from samples of two donors post exercise.
FIG. 14 shows a summary of test strip response to lactate for whole blood measurements from samples from the two donors.
Figure 15:
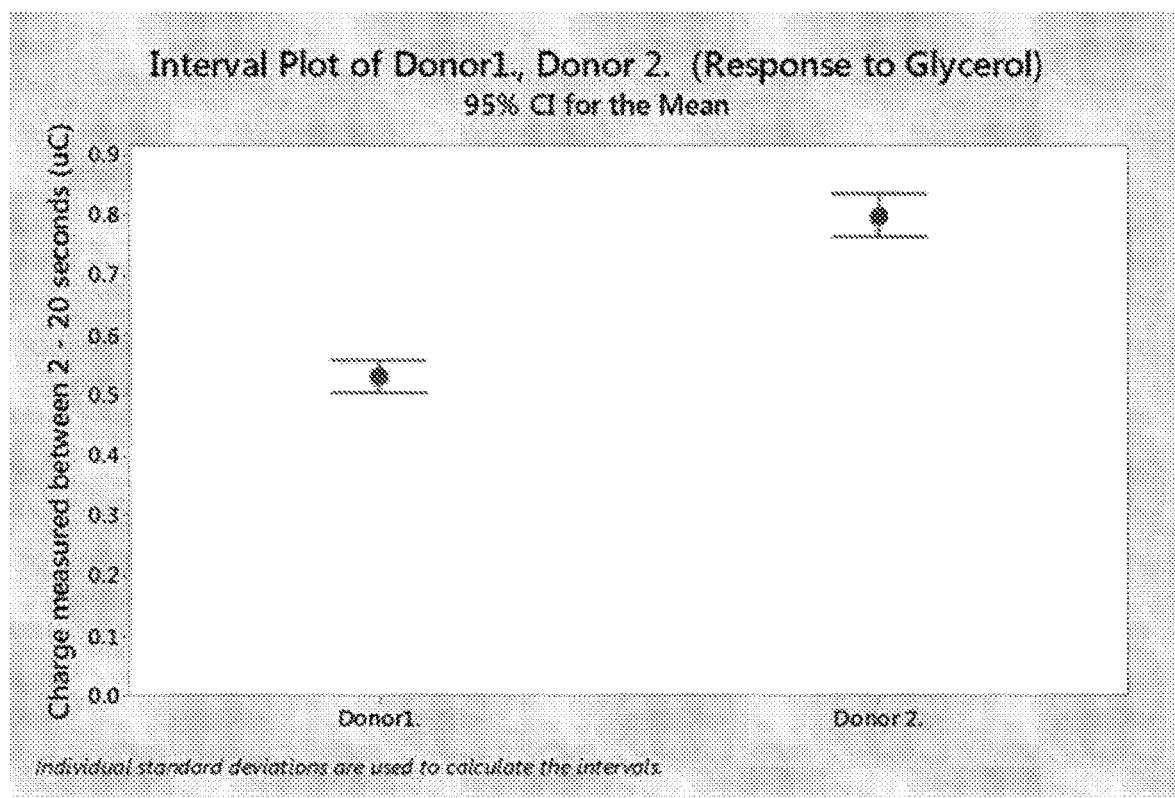
FIG. 15 shows a summary of test strip response to glycerol for whole blood measurements from samples from the two donors.

The corresponding strip responses (whole blood) for the two donors are shown in FIGS. 14 and 15. FIG. 14 shows a summary of the strip responses to lactate for Donor 1 and Donor 2. The means and the individual standard deviations are also represented. The measurements were carried out as described above. The lactate measurement was obtained at t=23 seconds, i.e. 3 seconds after the application of the 0.3V potential step. 10 individual strip measurements were carried out on each blood sample.

FIG. 15 shows a summary of the strip responses to glycerol for Donor 1 and Donor 2. The means and the individual standard deviations are also represented. The glycerol measurement was obtained by integrating the current between 2 and 20 seconds. 10 individual strip measurements were carried out on each blood sample.

In another specific example, in an electrochemical test device for measuring a concentration of lactate and a concentration of a second analyte, the sensing chemistry may be applied as described above in relation to FIG. 5. The electron transfer agent provided on the first working electrode 510 may be a ferricyanide anion such as potassium ferricyanide. The electron transfer agent on the second working electrode comprises ruthenium pentaammine chloride. Ruthenium pentaammine chloride has a standard redox potential of approximately −0.08V, whereas potassium ferricyanide has a standard redox potential of approximately 0.44V. Accordingly, the potential difference between the counter/reference electrode 520 and the second working electrode 530 is approximately 0.52V while the potential difference between the first working electrode 510 and the counter/reference electrode 520 is approximately 0V.

Ruthenium pentaammine chloride has a number of benefits as an electron transfer agent. In particular, ruthenium pentaammine chloride has a standard redox potential of approximately −0.08 Volts. The standard redox potential for the NAD(P)$^+$/NAD(P)H couple is approximately −0.315 Volts. Accordingly, ruthenium pentaammine chloride represents an overpotential with respect to the NAD(P)$^+$/NAD(P)H redox couple of approximately 0.235 Volts. In order to achieve the high level of sensitivity that is required to measure, for example, glycerol (typically 0.05 mM) or blood ketones such as β-hydroxybutyrate (typically 0.1 mM) it is useful to choose a mediator with a low redox potential so that any interference due to the oxidation of opportunist species is reduced. Ruthenium pentaammine chloride is thus a good candidate for use in an electrode for measuring glycerol or β-hydroxybutyrate. Furthermore, unlike some other compounds such as potassium ferricyanide, ruthenium pentaammine chloride does not react with surface amino acids present in the diaphorase which could lead to a deterioration of enzyme stability and therefore deterioration in electrode performance, and so the shelf life of the electrochemical test device is improved.

In another specific example, in an electrochemical test device for measuring a concentration of glucose and a concentration of β-hydroxybutyrate, the sensing chemistry may be applied as described above in relation to FIG. 5. The electron transfer agent provided on the first working electrode 510 is ruthenium pentaammine pyridine which has a standard redox potential of about 0.3V. The electron transfer agent on the second working electrode comprises ruthenium pentaammine chloride. Ruthenium pentaammine chloride has a standard redox potential of approximately −0.08V. Accordingly, the potential difference between the counter/reference electrode 520 and the second working electrode 530 is approximately 0.38V while the potential difference between the first working electrode 510 and the counter/reference electrode 520 is approximately 0V.

In another specific example, in an electrochemical test device for measuring a concentration of lactate in a fluid sample, the sensing chemistry may be applied in layers. In this example, the sensing chemistry for the first working electrode and the counter/reference electrode is lactate oxidase. The electron transfer agent in the layers coating the first working electrode and the counter/reference electrode is potassium ferricyanide which has a standard redox potential of approximately 0.44 V. The electron transfer agent provided in layer on the second working electrode is 1,2 naphthoquinone-4-sulphonate which has a standard redox potential of about −0.214V.

Instead of an NAD(P)$^+$-dependent dehydrogenase and cofactor, in this example a lactate oxidase is provided on the second electrode. No diaphorase is present at the second electrode. Accordingly, in this specific example, the electrochemical test device comprises two working electrodes, each provided with lactate oxidase for detecting lactate in a fluid sample, but with different electron transfer agents.

Due to the difference in the standard redox potentials of the mediators on the counter/reference electrode 520 and the second working electrode 530, an inherent thermodynamic potential difference between the electrodes may exist that is suitable for generating a current from electrocatalysis. The inherent thermodynamic potential difference between the second working electrode 530 and the counter/reference electrode is approximately 0.654V.

In another specific example, in an electrochemical test device for measuring a concentration of glucose in a fluid sample, the sensing chemistry may be applied in layers. In this example, the sensing chemistry for the first working electrode and the counter/reference electrode is glucose oxidase. The electron transfer agent in the layers coating the first working electrode and the counter/reference electrode is potassium ferricyanide. The electron transfer agent provided on the second working electrode is 1,2 naphthoquinone-4-sulphonate which has a standard redox potential of about −0.214V. The second working electrode is further provided with FAD-Glucose dehydrogenase. Accordingly, in this specific example, the electrochemical test device comprises two working electrodes, each provided with different sensing chemistry for detecting glucose in a fluid sample. Due to the different standard redox potentials of the mediators used for the second working electrode and the counter/reference electrode, a potential difference of approximately 0.654V may exist between the counter/reference electrode and the second working electrode suitable for generating a current from the fluid sample.

Figure 16:
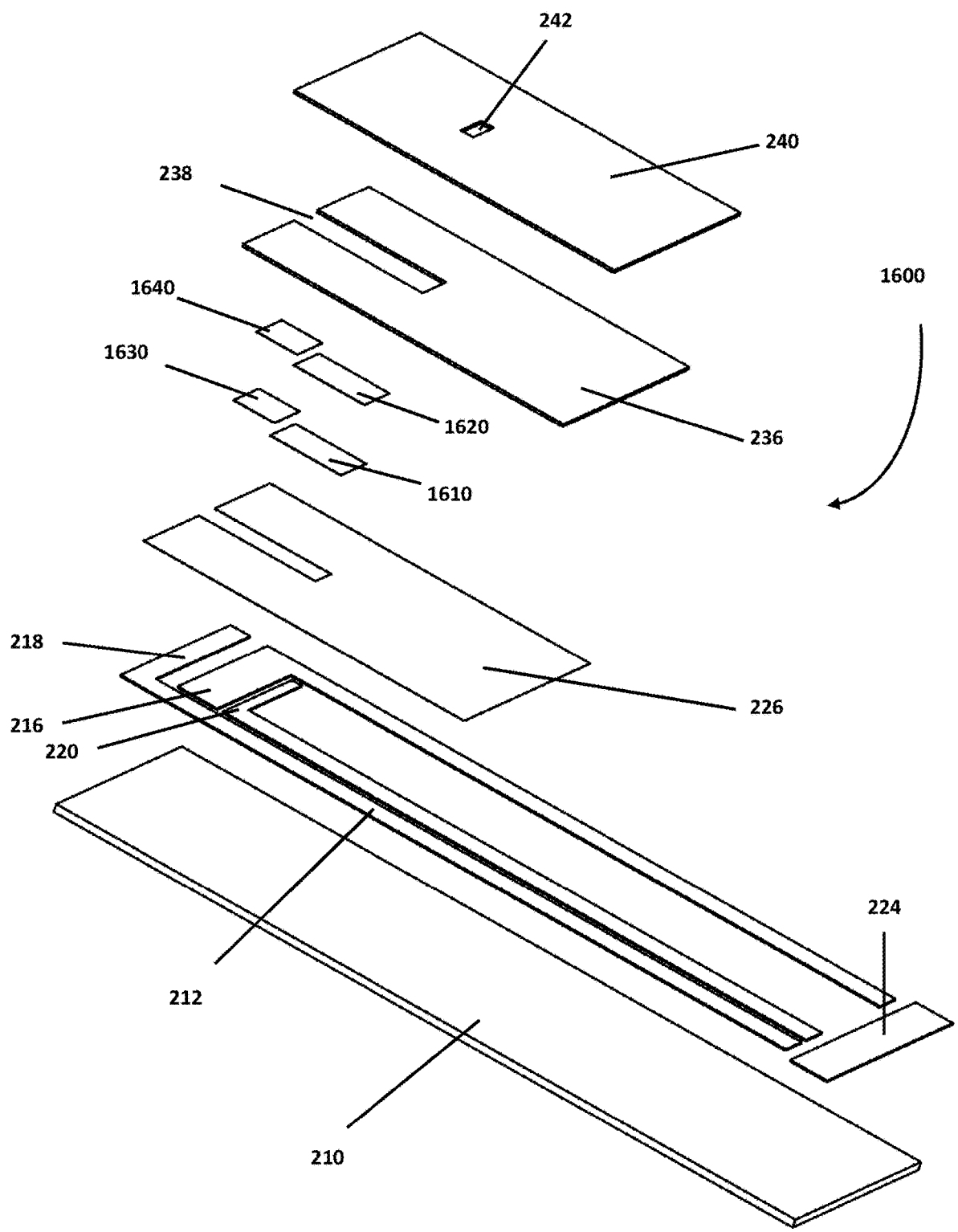
FIG. 16 shows an exploded view of an electrochemical test device.

FIG. 16 shows a perspective, exploded view of an electrochemical test device in the form of electrochemical test strip 1600 according to an example. The electrochemical test strip shown in FIG. 16 is formed of layers in much the same way as the electrochemical test strip of FIG. 2. As with the electrochemical test strip 200 of FIG. 2, this example will be described in relation to a received blood sample of around 0.5 μl in volume, although the electrochemical test strip 1600 could be used with any suitable fluid sample. The electrochemical test strip 1600 shown in FIG. 16 has an end-fill configuration.

The electrochemical test strip 1600 of FIG. 16 comprises a support layer or substrate 210. Above the substrate 210 is the conductor layer 212, which comprises a working electrode 218, a counter/reference electrode 216 and a fill-sufficiency detect electrode 220. Also shown is a switch-on bar 224 for activating a meter. Above the conductor layer 212 is an insulator layer 226 which defines an interaction area for the electrodes in the conductor layer 212. Sensing chemistry (reagent layers 1610, 1620, 1630 and 1640) is then applied to the exposed areas of the electrodes. Above the insulator layer 226 is a spacer layer 236 having a sample introduction channel 238. Above the spacer layer 236 is a cover layer 240 having a vent 242.

In this example, the sensing chemistry comprises four reagent layers 1610, 1620, 1630 and 1640 which are applied to exposed electrode interaction areas after the insulator layer 226 is formed. More or fewer reagent layers may be present. A first reagent layer 1610 is applied to the counter/reference electrode 216 and the fill-sufficiency detect electrode 220. An additional reagent layer 1620 is applied to the counter/reference electrode 216 and the fill-sufficiency detect electrode 220. The sensing chemistry for the counter/reference electrode 216 in this example comprises a first electron transfer agent having a first standard redox potential. The working electrode 218 is provided with reagent layers (1630, 1640). The sensing chemistry for the working electrode 218 comprises a second electron transfer agent having a second standard redox potential different to the first standard redox potential, and a reagent suitable for reacting with an analyte in a received blood sample. For example, the sensing chemistry for the working electrode 218 may comprise a diaphorase, the second electron transfer agent, an NAD(P)$^+$-dependent dehydrogenase for reacting with the analyte and a cofactor for the NAD(P)$^+$-dependent dehydrogenase. In a particular example, the first electron transfer agent may be potassium ferricyanide and the second electron transfer agent may be ruthenium pentaammine chloride.

In use, a blood sample is received by the electrochemical test device 1600. Due to the difference in standard redox potentials of the first electron transfer agent on the counter/reference electrode 216 and the second electron transfer agent on the working electrode 218, a potential difference may exist between the counter/reference electrode 216 and the working electrode 218 which is sufficient to generate a current in the received blood sample. Accordingly, as described above in relation to the previous examples, a measurement of a concentration of an analyte in the blood sample may be performed without the need to actively apply a potential difference across the working electrode 218 and the counter/reference electrode 216.

Variations of the described embodiments are envisaged, for example, the features of all the disclosed embodiments may be combined in any way.

For example, an electrochemical test device may contain more layers than those disclosed in the preceding description. For example, an electrochemical test device may further comprise one or more bonding layers for bonding together one or more of the layers disclosed above. Additionally, some of the layers are not always necessary. For example, the insulator layer may be absent from the examples discussed above. The spacer layer may define the interaction area of the electrodes of the conductor layer beneath. The spacer layer may perform the dual role of receiving a fluid sample through a capillary channel and defining an interaction area for combining the fluid sample with the conductor layer. For example, the spacer layer can, with appropriate adhesive, define the active area/interaction area of the electrodes.

In the examples of the electrochemical test device discussed above, a layer structure has been shown. The order in which each of the layers is formed may vary and any layer may, in some way, be configured so as to be in contact with any other layer.

The fluid sample may be a biological fluid. For example, the biological fluid may be blood, interstitial fluid, plasma, sweat, urine, lachrymal fluid, saliva or breath condensate. The one or more analytes may be any analyte(s) found in the fluid sample. For example, the analytes may be one or more of glucose, lactate, glycerol, cholesterol, or a ketone body such as β-hydroxybutyrate.

The electrochemical test strip may be configured to detect any combination of analytes so long as a suitable sensing chemistry is used. Example combinations include lactate and glycerol; lactate and β-hydroxybutyrate; lactate and glucose; glucose and glycerol; lactate and lactate; glucose and β-hydroxybutyrate; and glycerol and β-hydroxybutyrate to name a few. Further working electrodes may be provided allowing higher numbers of analytes to be measured. For example, the electrochemical test strip may be configured to detect glucose, glycerol and β-hydroxybutyrate; lactate, glycerol and glucose; or lactate, glycerol and β-hydroxybutyrate.

The electrochemical test device may be any suitable electrochemical test device. The electrochemical test device may be a test strip. In some examples the electrochemical test device may comprise a patch. Electrochemical test devices such as patches typically comprise a subcutaneous fluid extraction set and sensing chemistry for interaction with the one or more analytes. The electrochemical test device may be a monitoring component which transmits an output signal to a separate device such as a meter, either wirelessly or through a wired connection. The electrochemical test device may comprise a continuous monitoring device or a semi-continuous monitoring device.

The electrochemical test device may be suitable for testing for multiple analytes or biometrics. For example, the conductor layer may comprise a number of working electrodes, each working electrode featuring different sensing chemistry for detecting a different analyte. In particular, for each analyte there may be a dedicated working electrode of the conductor layer coated in a particular reagent suitable for reacting with the analyte.

In the examples discussed above in relation to FIGS. 2 and 16, the electrochemical test devices had an end-fill configuration. In other embodiments, an electrochemical test device has a side-fill configuration i.e. the fluid sample is received at the side of the electrochemical test device.

The electrochemical test device may be suitable for measuring any fluid sample volume and may be of a suitable corresponding size for the volume. For example the electrochemical test devices described in relation to FIGS. 2 and 16 were arranged to receive approximately 0.5 μl of blood. The electrochemical test device may be scaled so as to receive other volumes including, for example, between 0.5 μl and 5 μl of a fluid, or between 0.5 μl and 1 μl of a fluid. The electrochemical test device may be scaled so as to receive less than 0.5 μl of a fluid, for example around 0.2 μl or around 0.3 μl.

Although in the discussion above in relation to FIGS. 2 and 16 a fill-sufficiency detect electrode 220 was present, the fill-sufficiency detect electrode need not be present. Additionally, the fill-sufficiency detect electrode may or may not be coated in one or more reagent layers.

In the examples provided above, the conductor layer and the insulator layer are printed layers. The conductor layer and the insulator layer may be supplied using any suitable manufacturing technique. These include forms of printing, for example, screen printing, lithographic printing or tomographic printing. The conductor layer and the insulator layer need not be provided in the same way. Other suitable manufacturing techniques include etching, and/or sputtering, chemical vapour deposition or physical vapour deposition.

A conductor layer may be formed of any suitable conductor. For example, the conductor layer may be formed from a carbon based paste, such as a carbon/graphite paste, including graphene. The conductor layer may be formed of one or more metal based paste such as a gold, platinum or silver paste. Although the conductor layer 212 described above in relation to FIG. 2 comprises carbon-based ink, the conductors need not be formed from carbon based ink. For example, the electrodes may be formed of silver (Ag) or silver/silver chloride (Ag/AgCl). In some examples, the electrodes are formed of different conducting materials. The one or more working electrodes may, for example, be formed of carbon based ink whereas the counter/reference electrode may be formed of silver (Ag) or silver/silver chloride (Ag/AgCl).

The conductor layer may be of any suitable thickness. For example, the conductor layer may have a thickness greater than or equal to 0.005 mm and less than or equal to 0.030 mm.

The ordering of the electrodes on the electrochemical test device may be altered for efficiency. In one preferable option, an electrode for an analyte for which a weak signal is expected (for example glycerol which is often present in very low concentrations in blood) may be positioned closer to the entrance of the sample introduction chamber than an electrode for an analyte such as glucose or lactate which is usually present in higher concentrations.

The insulator layer may be formed of any suitable insulating material. For example, dielectric/insulation inks may be polymer loaded inks that are thermoplastic, thermoset or UV cured and that, when dried or cured, form a contiguous non-conductive layer. Examples include, Loctite EDAG PF 021 E&C and DuPont 5018.

In the examples discussed above, a polyester substrate layer was featured. Suitable substrate materials include polyester, polyimide, polystyrene, PVC, polycarbonate, glass and ceramic. When other layers are to be printed onto the substrate layer, the substrate layer has to be suitably printable for the chosen inks. The substrate must also be non-conductive. Typical thicknesses of the substrate layer range from 0.1 mm to 0.5 mm e.g. 0.35 mm. Glass and ceramic can be thicker as these are easier to handle with increased thickness. Thinner polymer substrates may be more difficult for the end user to use. Thicker substrates may offer some handling benefits.

The spacer layer may be formed of any suitable material. For example, the spacer layer may be made from a polyester core with a thin layer of PSA (Pressure Sensitive Adhesive) on either side. These adhesives can be the same or different depending on which layer is to be adhered to which side of the spacer layer.

Although in the examples above the thickness of the spacer layer was 0.1 mm, the thickness may vary. A typical range for the spacer layer thickness is 0.005-0.030 mm. Lower thicknesses may affect sensor performance and higher thicknesses would increase the volume of the sample introduction channel. A thickness of an adhesive on the spacer layer may contribute to the rigidity of the spacer layer.

Typically a spacer layer has a high volume resistivity. For example the volume resistivity may be greater than $1 \times 10^9$ Ωcm.

Other variations of the spacer layer are envisaged.

The sample introduction chamber may be provided along the longitudinal axis of the electrochemical device. The sample introduction chamber may be provided along the transverse axis of the electrochemical test device.

The vent may be of any suitable configuration for venting air from the sample introduction chamber. For example, the vent may comprise an air passageway in the cover. The vent may comprise an air passageway in the spacer layer. Optionally, air may be vented from the sample introduction chamber through one or more air passageways below the spacer layer, such as through the conductor layer or the insulator layer.

Sensing chemistry may include any suitable mediator. In the examples described above, a ruthenium-based electron transfer agent has been disclosed for use with the second working electrode. Other suitable mediators may be osmium-based. For example, osmium phendione is a suitable mediator having a low standard redox potential. As another example, $Os(4,4'\text{-dimethyl-}2,2'\text{-bipyridine})_2$ is a suitable mediator having a low standard redox potential.

An electron transfer agent for a working electrode may comprise a suitable quinone, for example a naphthoquinone derivative. The naphthoquinone derivative may be a 1,2 naphthoquinone derivative or a 1,4 naphthoquinone derivative. For example, the electron transfer agent may comprise 1,4 naphthoquinone-2-mercapto methyl carboxylic acid which has a standard redox potential of around −0.355V. The electron transfer agent may comprise 1,4 naphthoquinone-2-mercapto benzoic acid, which has a standard redox potential of around −0.345V. The electron transfer agent may comprise 1,2 naphthoquinone-4-sulphonate, which has a standard redox potential of around −0.214V. The electron transfer agent may comprise 1,4 naphthoquinone-2-mercapto methyl sulphonate. Also other suitable isomers of the above listed compounds are known which have similarly low standard redox potentials within the desired range.

In the examples above, the sensing chemistry is applied to each of the working electrodes as two reagent layers. There may be more than two reagent layers for each working electrode. There may be only one reagent layer for each working electrode.

In the discussion above in relation to FIG. 5, the first working electrode 510 and the counter/reference electrode 520 are provided with reagent layers comprising an electron transfer agent and a suitable reagent for reacting with a first analyte. The electron transfer agent and the analyte-sensitive reagent may be provided in the same layer or may be provided in different layers.

With reference to the sensing chemistry for the second working electrode 530 of FIG. 5, the diaphorase and electron transfer agent were disclosed as being in the layer adjacent the second working electrode. The diaphorase and the electron transfer agent may be provided in the same layer or may be provided in different layers. Additionally, the NAD(P)$^+$-dependent dehydrogenase and the cofactor respectively may be provided in the same layer or may be provided in different layers. Other combinations of the reagents on the second working electrode are envisaged.

In the disclosure above, an NAD(P)$^+$-dependent dehydrogenase for reacting with an analyte was described. Examples of suitable NAD(P)$^+$-dependent dehydrogenases include glycerol dehydrogenase, glycerol-3-phosphate dehydrogenase, D-3-hydroxybutyrate dehydrogenase, cholesterol dehydrogenase, lactate dehydrogenase, D-Lactate dehydrogenase, malate dehydrogenase, alcohol dehydrogenase and leucine dehydrogenase.

Whilst the above examples have been described primarily in the context of an electrochemical test device for measuring a concentration of an analyte in a bodily fluid, it may equally be used in other fields, for example in health and fitness, food, drink, bio-security applications and environmental sample monitoring. The examples described herein may equally be used in the context of animal/veterinary medicine and fitness (including dogs and horses).

The above embodiments have been described by way of example only, and the described embodiments are to be considered in all respects only as illustrative and not restrictive. It will be appreciated that variations of the described embodiments may be made without departing from the scope of the invention.

The invention claimed is:

1. An electrochemical test device for use in determining a concentration of each of a first analyte and a second analyte in a fluid sample, the electrochemical test device comprising a set of electrodes including a first working electrode having sensing chemistry for the first analyte, a second working electrode having sensing chemistry for the second analyte, and a counter/reference electrode configured to establish a current between each of the first and second working electrode, wherein:
    the first analyte is lactate and the sensing chemistry for the lactate comprises lactate oxidase and an electron transfer agent;
    the sensing chemistry for the second analyte comprises a diaphorase, a second electron transfer agent having a second redox potential, an NAD(P)+-dependent dehydrogenase and a cofactor for the NAD(P)+-dependent dehydrogenase; and
    the counter/reference electrode is provided with a third electron transfer agent having a third redox potential, wherein the third standard redox potential is higher than the second standard redox potential by at least 0.2V and wherein the first standard redox potential is substantially the same as the third standard redox potential.

2. An electrochemical test device according to claim 1, wherein the second analyte is glycerol and the NAD(P)+-dependent dehydrogenase is glycerol dehydrogenase; or
    wherein the second analyte is β-hydroxybutyrate and the NAD(P)+-dependent dehydrogenase is β-hydroxybutyrate dehydrogenase; or wherein the second analyte is glucose and the NAD(P)+-dependent dehydrogenase is NAD+-glucose dehydrogenase.

3. An electrochemical test device according to claim 1, wherein the electron transfer agent for the first working electrode and the electron transfer agent for the second working electrode are different electron transfer agents; and optionally
wherein the electron transfer agent for the first working electrode (the "first" electron transfer agent) has a first standard redox potential, the electron transfer agent for the second working electrode (the "second" electron transfer agent) has a second standard redox potential, and the third electron transfer agent has a standard redox potential; and
wherein the third standard redox potential is higher than the second standard redox potential by at least 0.3V.

4. An electrochemical test device according to claim 3, wherein the third standard redox potential is in the range of −0.12V to 0.58V; and/or
wherein the second standard redox potential is in the range of −0.52V to 0.18V and/or
wherein the first electron transfer agent is the same as the third electron transfer agent; and/or
wherein the electron transfer agent for the first working electrode is a ferricyanide anion; and/or
wherein the sensing chemistry for the first working electrode is disposed in at least one layer, wherein each layer comprises the lactate oxidase and the electron transfer agent for the first working electrode; and optionally
wherein the sensing chemistry for the first working electrode is disposed in two layers.

5. An electrochemical test device according to claim 3, wherein the sensing chemistry for the second working electrode is disposed in at least one layer, wherein each of the at least one layer comprises the diaphorase, the electron transfer agent for the second working electrode, the NAD(P)+-dependent dehydrogenase and the cofactor for the NAD(P)+-dependent dehydrogenase; and/or
wherein the sensing chemistry for the second working electrode is disposed in layers including a layer adjacent the second working electrode, and wherein the layer adjacent the second working electrode comprises the diaphorase; and
wherein the layer adjacent the second working electrode also comprises the electron transfer agent; and
wherein the layers include a layer which is not adjacent the second working electrode, and the layer which is not adjacent the second working electrode comprises the NAD(P)+-dependent dehydrogenase and optionally
wherein the layer not adjacent the second working electrode also comprises the cofactor.

6. An electrochemical test device according to claim 3, wherein the layers of sensing chemistry for the second working electrode are disposed in two layers; and/or
wherein the electron transfer agent for the second working electrode is ruthenium hexaamine trichloride; and/or
wherein the electron transfer agent for the second working electrode is a naphthoquinone derivative; and/or
wherein the electron transfer agent for the first working electrode is a ferricyanide anion and the electron transfer agent for the second working electrode is ruthenium hexaamine trichloride; or
wherein the electron transfer agent for the first working electrode is a ferricyanide anion and the electron transfer agent for the second working electrode is ruthenium pentaamine chloride; and/or
wherein the second working electrode is positioned nearer an entrance to the sample introduction chamber of the electrochemical test device than the first working electrode.

7. An electrochemical test device according to claim 1 wherein the electron transfer agent for the second working electrode is a ruthenium- or osmium-based electron transfer agent; and optionally
wherein the ruthenium- or osmium-based electron transfer agent is a complex of formula I

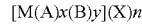   Formula I wherein
M is ruthenium or osmium;
A is an amine ligand;
each B is a ligand different to A;
x is an integer selected from 1 to 5;
y is an integer selected from 1 to 5;
x+y is 6 or 8;
n is an integer selected from 1 to 6;
X is any suitable counterion.

8. An electrochemical test device according to claim 7, wherein M is ruthenium; and/or
wherein B is halide, or optionally substituted heteroaryl; and
optionally
wherein B is chloride; or
wherein B is an optionally substituted pyridine; or
wherein B is pyridine or 4-methyl pyridine.

9. An electrochemical test device according to claim 7, wherein the oxidation state of the metal is selected to be 2+ or 3+; and/or
wherein the counterion X is selected from F$^-$, Cl$^-$, Br$^-$, I$^-$, PF$_6^-$; or
wherein the ruthenium complex is [Ruthenium$^{III}$(NH$_3$)5Cl]X; and
optionally wherein the ruthenium complex is [Ruthenium$^{III}$(NH$_3$)5Cl].2Cl.

10. An electrochemical test device according to claim 1 wherein the electron transfer agent for the first working electrode and the electron transfer agent for the second working electrode have standard redox potentials which are substantially the same; and optionally
wherein the electron transfer agent for the first working electrode and the electron transfer agent for the second working electrode is the same electron transfer agent; and optionally
wherein the electron transfer agent for the first working electrode and the electron transfer agent for the second working electrode is a quinone; and/or
wherein the electron transfer agent for the first working electrode and the electron transfer agent for the second working electrode is a naphthoquinone derivative; and/or
wherein the electron transfer agent for the first working electrode and the electron transfer agent for the second working electrode is a 1,2 naphthoquinone derivative or a 1,4 naphthoquinone derivative; and optionally
wherein the naphthoquinone derivative is 1,4 naphthoquinone-2-mercapto methyl carboxylic acid; or
wherein the naphthoquinone derivative is 1,4 naphthoquinone-2-mercapto benzoic acid; or
wherein the naphthoquinone derivative is 1,2 naphthoquinone-4-sulphonate; or wherein the naphthoquinone derivative is 1,4 naphthoquinone-2-mercapto methyl sulphonate.

11. An apparatus configured to determine the concentration of an analyte in a fluid sample applied to an electrochemical test device according to claim 1.

12. A method of determining a concentration of a first analyte in a fluid sample and a concentration of a second analyte in the fluid sample, wherein an electrochemical test device is used, the device comprising a set of electrodes comprising a first working electrode, a second working electrode and a counter/reference electrode configured to establish a current between each of the first and second working electrode, wherein the first working electrode is provided with first sensing chemistry for the first analyte, the first sensing chemistry including a first electron transfer agent, and wherein the second working electrode is provided with second sensing chemistry for the second analyte, the second sensing chemistry including a second electron transfer agent, wherein the counter/reference electrode is provided with a third electron transfer agent, wherein the first electron transfer agent has a first standard redox potential, the second electron transfer agent has a second standard redox potential and the third electron transfer agent has a third standard redox potential, wherein the third standard redox potential is higher than the second standard redox potential by at least 0.2V, wherein the first standard redox potential is substantially the same as the third standard redox potential, the method comprising:
- operating in a fuel cell mode for a first time period in which the difference between the second standard redox potential and the third standard redox potential causes current to flow from the second working electrode to the counter/reference electrode, wherein the first time period serves as a poise delay period for the first working electrode;
- after the first time period, applying a potential difference for a second time period between the first working electrode and the counter/reference electrode;
- determining the concentration of the second analyte based on an output signal generated from the current that flows between the second working electrode and the counter/reference electrode in the first time period; and
- determining the concentration of the first analyte based on an output signal generated from the current that flows between the first working electrode and the counter/reference electrode in the second time period.

13. A method according to claim 12, wherein the first electron transfer agent is the same as the third electron transfer agent; and/or
- wherein the first time period is between 1 and 30 seconds, optionally between 5 and 20 seconds, optionally between 15 and 20 seconds, optionally between 5 and 10 seconds; and/or
- wherein determining the concentration of the second analyte comprises integrating at least a portion of the output signal; and/or
- wherein the potential difference is between 0.1 and 0.5 Volts, optionally between 0.2 and 0.4 Volts, optionally between 0.25 and 0.35 Volts; and/or
- wherein the first analyte and the second analyte are the same analyte; and optionally
- wherein the first sensing chemistry and second sensing chemistry comprise different enzymes; and/or
- wherein one of the first and second sensing chemistry comprises an oxidase and the other of the first and second sensing chemistry comprises a dehydrogenase; and optionally
- wherein the oxidase is glucose oxidase and the dehydrogenase is FAD-glucose dehydrogenase or PQQ-glucose dehydrogenase.

14. A method according to claim 13, wherein the first analyte and the second analyte are different analytes; and optionally
- wherein the first sensing chemistry and second sensing chemistry comprise different enzymes; and/or
- wherein the first analyte is lactate and second analyte is glycerol; or wherein the first analyte is lactate and second analyte is β-hydroxybutyrate; or
- wherein the first analyte is lactate and second analyte is glucose; or wherein the first analyte is glucose and second analyte is glycerol; or wherein the first analyte is glucose and second analyte is β-hydroxybutyrate; and/or
- wherein one of the first and second sensing chemistry comprises an oxidase and the other of the first and the second sensing chemistry comprises a dehydrogenase.

15. An apparatus for determining a concentration of a first analyte a fluid sample and a concentration of a second analyte in the fluid sample, the apparatus comprising:
- circuitry for receiving an output signal generated from a fluid sample;
- a memory storing instructions to perform the method of claim 12; and
- a processor configured to perform the instructions stored in the memory.

16. A machine-readable medium having instructions stored thereon, the instructions being configured such that when read by a machine the instructions cause the method of claim 12 to be carried out.

17. An electrochemical test device for use in determining a concentration of a first analyte in a fluid sample and a concentration of a second analyte in the fluid sample, the device comprising a set of electrodes comprising a first working electrode, a second working electrode and a counter/reference electrode configured to establish a current between each of the first and second working electrode, wherein the first working electrode is provided with first sensing chemistry for the first analyte, the first sensing chemistry including a first electron transfer agent, and wherein the second working electrode is provided with second sensing chemistry for the second analyte, the second sensing chemistry including a second electron transfer agent, wherein the counter/reference electrode is provided with a third electron transfer agent, wherein the first electron transfer agent has a first standard redox potential, the second electron transfer agent has a second standard redox potential and the third electron transfer agent has a third standard redox potential, wherein the third standard redox potential is higher than the second standard redox potential by at least 0.2V, and wherein the first standard redox potential is substantially the same as the third standard redox potential.

18. An electrochemical test device according to claim 17, wherein the first electron transfer agent is the same as the third electron transfer agent; or
- wherein the third standard redox potential is higher than the second standard redox potential by at least 0.3V; and optionally
- wherein the third standard redox potential is higher than the second standard redox potential by at least 0.4V; and/or
- wherein the first analyte and the second analyte are the same analyte; and optionally
- wherein the first sensing chemistry and second sensing chemistry comprise different enzymes; and/or wherein one of the first and second sensing chemistry comprises an oxidase and the other of the first and second sensing chemistry comprises a dehydrogenase; and optionally wherein the oxidase is glucose oxidase and the dehydrogenase is FAD-glucose dehydrogenase or PQQ-glucose dehydrogenase.

19. An electrochemical test device according to claim 17 wherein the first analyte and the second analyte are different analytes; and optionally wherein the first sensing chemistry and second sensing chemistry comprise different enzymes; and/or wherein the first analyte is lactate and second analyte is glycerol; or wherein the first analyte is lactate and second analyte is β-hydroxybutyrate; or wherein the first analyte is lactate and second analyte is glucose; or wherein the first analyte is lactate and second analyte is glucose; or wherein the first analyte is glucose and second analyte is glycerol; or wherein the first analyte is glucose and second analyte is β-hydroxybutyrate; and/or wherein one of the first and second sensing chemistry comprises an oxidase and the other of the first and second sensing chemistry comprises a dehydrogenase.

20. An electrochemical test device according to claim 17, wherein the sensing chemistry for each of the first and second working electrodes is disposed in at least one layer.

* * * * *

UNITED STATES PATENT AND TRADEMARK OFFICE
CERTIFICATE OF CORRECTION

PATENT NO. : 10,788,442 B2  
APPLICATION NO. : 15/569742  
DATED : September 29, 2020  
INVENTOR(S) : Marco Cardosi et al.

Page 1 of 1

It is certified that error appears in the above-identified patent and that said Letters Patent is hereby corrected as shown below:

On the Title Page

Item (22) PCT Filed:  
Reads "Apr. 27, 2016"  
Should read --Apr. 28, 2016--

Signed and Sealed this  
Nineteenth Day of January, 2021

Andrei Iancu  
*Director of the United States Patent and Trademark Office*